United States Patent
Le Poole et al.

(10) Patent No.: US 10,829,526 B2
(45) Date of Patent: Nov. 10, 2020

(54) METHOD OF TREATING VITILIGO USING MUTANT HSP70I

(71) Applicant: Loyola University of Chicago, Maywood, IL (US)

(72) Inventors: I. Caroline Le Poole, Downers Grove, IL (US); Jose Alejandro Guevara, Chicago, IL (US); Andrew Zloza, Chicago, IL (US)

(73) Assignee: LOYOLA UNIVERSITY OF CHICAGO, Chicago, IL (US)

( * ) Notice: Subject to any disclaimer, the term of this patent is extended or adjusted under 35 U.S.C. 154(b) by 212 days.

(21) Appl. No.: 15/791,609

(22) Filed: Oct. 24, 2017

(65) Prior Publication Data
US 2018/0066030 A1    Mar. 8, 2018

Related U.S. Application Data

(62) Division of application No. 14/127,579, filed on Jul. 24, 2014, now abandoned.

(60) Provisional application No. 61/529,050, filed on Aug. 30, 2011.

(51) Int. Cl.
| | |
|---|---|
| *A61K 39/008* | (2006.01) |
| *C07K 14/47* | (2006.01) |
| *A01K 67/027* | (2006.01) |
| *A61K 38/08* | (2019.01) |
| *A61K 48/00* | (2006.01) |

(52) U.S. Cl.
CPC ...... *C07K 14/4705* (2013.01); *A01K 67/0276* (2013.01); *A61K 38/08* (2013.01); *C07K 14/47* (2013.01); *A01K 2217/075* (2013.01); *A01K 2227/105* (2013.01); *A01K 2267/0325* (2013.01); *A61K 48/005* (2013.01)

(58) Field of Classification Search
None
See application file for complete search history.

(56) References Cited

FOREIGN PATENT DOCUMENTS

WO    WO-2009036349 A1 *  3/2009  ............. C07K 14/47

OTHER PUBLICATIONS

Nieland, J.D., et al.J. Invest.Derm. 2020;130:Suppl. 2, S4, Abstract 19.*
Jose A. Guevara-Patino, Manuel E. Engelhorn, Mary Jo Turk, Calilian Liu, Fei Duan, Gabrielle Rizzuto, Adam D. Cohen, Taha Merghoub, Jedd D. Wolchok, and Alan N. Houghton; "Optimization of a self antigen for presentation of multiple epitopes in cancer immunity"; The Journal of Clinical Investigation, vol. 116, No. 5, May 2006.
Cecele J. Denman, James McCracken, Vidhya Hariharan, Jared Klarquist, Kepa Oyarbide-Valencia, Jose A. Guevara-Patino, and I. Caroline Le Poole, "HSP70i Accelerates Depigmentation in a Mouse Model of Autoimmune Vitiligo"; J Invest Dermatal, Aug. 2008; 128 (8): 2041-2048; doi: 10.1038/jid.2008.45.

* cited by examiner

*Primary Examiner* — G. R. Ewoldt
(74) *Attorney, Agent, or Firm* — Marshall, Gerstein & Borun LLP

(57) ABSTRACT

Methods of treating autoimmune diseases, such as vitiligo, by using compositions comprising DNA encoding a variant inducible heat shock protein 70 (HSP70i) having a mutation in the dendritic cell binding region thereof (HSP70i435-447) or an isolated variant gene product in the form of HSP70i with a modification in the dendritic cell activating region thereof (HSP70i435-447).

6 Claims, 22 Drawing Sheets

Specification includes a Sequence Listing.

Wild-type Mice

CD8 KO Mice

METHOD OF TREATING VITILIGO USING MUTANT HSP70I

CROSS REFERENCE TO RELATED APPLICATIONS

This is a division patent application of co-pending U.S. patent application Ser. No. 14/127,579, filed Aug. 30, 2012, which claims the benefit of U.S. Provisional Application No. 61/529,050, filed Aug. 30, 2011. The contents of these prior applications are incorporated herein by reference.

STATEMENT REGARDING FEDERALLY SPONSORED RESEARCH

This invention was made with government support under Grant/Contract No. AR054749 awarded by the National Institute of Health. The government has certain rights in the invention.

BACKGROUND OF THE INVENTION

The present invention generally relates to treatments for autoimmune diseases. More particularly, this invention relates to the use of variant peptides representing a sequence of amino acids found in heat shock protein 70 (HSP70) to treat autoimmune diseases such as vitiligo.

Vitiligo is an autoimmune disorder of the skin presenting with depigmenting lesions, affecting approximately 0.5% of the world's population. vitiligo lesions are milky-white patches that can increase in shape and size over time and the distribution of these lesions defines disease classification. In particular among dark skinned individuals, emotional effects can range from mild embarrassment to severe social anxiety reinforcing the impact of vitiligo on a patient's quality of life. Meanwhile, treatment opportunities are very limited and largely unsuccessful.

Support for vitiligo as an autoimmune disease is provided by infiltrates of T cells and macrophages described for skin of actively depigmenting patients. Circulating autoantibodies towards melanocyte antigens have also been detected. Mutations in genes associated with autoimmunity have been identified by family studies, such as a human leukocyte antigen (HLA) system which defines antigen presentation, and vitiligo melanocytes often display anomalies in gene expression of proteins essential in antigen processing and protein folding. In addition, vitiligo patients often develop other autoimmune disorders such as thyroid disease, pernicious anemia, addison's disease, and lupus. These and several other autoimmune disorders have been linked with HLA molecules, particularly HLA class II (HLA-DR). Patients with HLA molecules susceptible to binding autoantigens have higher frequencies of autoreactive T cells in their circulation. As often observed in autoimmune-affected tissue, perilesional skin from vitiligo patients displays elevated expression of HLA-DR.

Immunohistochemical staining of vitiligo skin with a panel of antibodies reactive with different melanocyte-specific features has revealed in previous studies that depigmentation is due to a loss of melanocytes rather than a disruption of melanin production. The role of such infiltrates in mediating an immune response specifically to melanocytes is supported by increased frequencies of T cells reactive with melanocyte antigens in both the skin and circulation of vitiligo patients. Increased infiltration of T cells in vitiligo skin involves primarily CD8+, that is, cytotoxic T cells pointing to a Th1 mediated immune response.

Patients frequently indicate that their vitiligo lesions were augmented or initiated under the influence of stress, including triggering factors such as UV overexposure, mechanical trauma or contact with bleaching phenols. Psychological stress may also contribute to vitiligo development. Such precipitating factors then translate into an autoimmune response specifically targeting melanocytes. To further understand this, stress can directly affect the immune system, as evidenced by changes in CD4+/CD8+ T cell ratios following stress mediated activation of β-adrenergic receptors of the sympathetic nervous system. Upon activation of the sympathetic nervous system, heat shock proteins (HSP) released into the extracellular milieu can drive the immune response. Thus HSPs can mediate the translation between causative stress factors and the autoimmune response to follow.

HSP70 is a family of proteins including constitutive HSP70 and inducible HSP70 (HSP70i). HSP70i is among cytoplasmic chaperones upregulated in response to temperature changes and other forms of stress. HSP70i is involved in maintaining molecular and cellular integrity, preventing protein misfolding and subsequent apoptosis. Extracellular HSP70i in turn serves as an alarm signal to the immune system by supporting uptake, processing and presentation of chaperoned antigens in the context of MHC class I and II, and invoking both the innate and adaptive responses. Dendritic cell (DC) activation allows for subsequent recruitment of CD8+ T cells from draining lymph nodes reactive with chaperoned proteins and peptides.

The unique role of HSP70i in precipitating autoimmunity may be better understood considering that HSP70i is actively secreted by living cells. Melanocytes established from non-lesional vitiligo skin treated with skin bleaching 4-tertiary butyl phenol (4-TBP) has been shown in previous studies to increase secretion of HSP70i. The same stress also confers sensitivity to DC-mediated cytotoxicity through tumor necrosis factor-related apoptosis-inducing ligand (TRAIL). HSP70i is released into the circulation via necrosis, or secreted by active transport through exosomal release. Similar to the proposed mechanism for inducing autoimmunity in vitiligo, in vivo studies have shown that HSP70i secreted from tumors confer anti-tumor responses via the peptides they chaperone.

The role HSP70 has on the immune response can in part be explained by the activation of DCs). This is supported by evidence that HSPs chaperoning antigenic peptides can induce DC-mediated activation of cytotoxic T lymphocytes (CTLs). In addition, HSPs enhanced the presentation of tyrosinase peptide to specific CTLs. HSP70 also activates DCs directly, as indicated by upregulation of the maturation markers CD40, CD83, and CD86. A 20-mer peptide sequence within microbial HSP70 has been assigned an immune regulatory function. HSP70 is believed to bind multiple receptor molecules on the DC membrane including TLR4, TLR2, CD14, CD91, and CD40. Antibodies that bind these receptors are generally capable of activating DCs as well. Thus, inhibiting DC activation by blocking receptors from binding HSP70 is not expected to meet with success as a measure to prevent autoimmune responses.

In view of the above, it can be appreciated that improved methods of treating patients with autoimmune diseases, such as vitiligo, are needed.

BRIEF DESCRIPTION OF THE INVENTION

The present invention provides compositions and methods of treatment suitable for treating autoimmune diseases, such as vitiligo, by using variant peptides representing a sequence of amino acids found in heat shock protein 70 (HSP70).

According to a first aspect of the invention, a method of treating autoimmune diseases, such as vitiligo, is provided that includes administering to a subject a composition comprising DNA encoding a variant inducible heat shock protein 70 (HSP70i) having a mutation in the dendritic cell binding region thereof (HSP70i435-447) or an isolated variant gene product in the form of HSP70i with a modification in the dendritic cell activating region thereof (HSP70i435-447).

A technical effect of the invention is the ability to treat autoimmune diseases, such as vitiligo by reducing activation of dendritic cells. In particular, it is believed that, treating a patient with a composition comprising DNA encoding a variant inducible heat shock protein 70 (HSP70i) having a mutation in the dendritic cell binding region thereof (HSP70i435-447) or an isolated variant gene product in the form of HSP70i with a modification in the dendritic cell activating region thereof (HSP70i435-447) will reduce activation of dendritic cells and thereby reduce the symptoms of autoimmune diseases.

Other aspects and advantages of this invention will be better appreciated from the following detailed description.

DETAILED DESCRIPTION OF THE INVENTION

The present invention will be described in terms of methods for treatment of autoimmune diseases. In one aspect of the invention, a mutant inducible heat shock protein 70 is used to treat depigmintation resulting from the autoimmune disease vitiligo.

Vaccines including melanocyte-specific antigens in combination with HSP70 have been shown in previous studies to elicit immune responses towards tumorigenic and healthy melanocytes. Whereas intracellular heat shock proteins serve a cytoprotective function, upon secretion, an inducible isoform of HSP70 (HSP70i; SEQ ID NO: 1) functions as a chaperokine, eliciting innate and adaptive immune responses to surrounding tissue. Under stressful conditions, secreted, HSP70i is believed to serve as an adjuvant in vitiligo, binding melanocytic antigens to be processed by antigen presenting cells (APC) and eliciting autoimmune responses to melanocytes in active disease. HSP70i (SEQ ID NO: 1) may also activate dendritic cell (DC) directly through specific receptor binding, leading to production of various cytokines such as IL-12, and IFN-γ and the subsequent activation and recruitment of effector cells from draining lymph nodes. Thus, the identification of a peptide within HSP70 crucial to eliciting autoimmunity would open doors to preventing the causative chain of events leading to depigmentation in vitiligo.

As previously discussed, heat shock protein 70 (HSP70) as well as various other heat shock proteins, have been implicated in DC activation. It is believed that inhibiting DC activation by blocking receptors from binding HSP70 is not expected to meet with success as a measure to prevent autoimmune responses. Therefore, moieties within HSP70 capable of binding and activating DCs were investigated in order to modulate the development of autoimmune vitiligo. Specifically, HSP70i was investigated to determine whether its role in vitiligo is unique or redundant in order to justify targeting a single stress protein as a treatment measure for autoimmune disease. HSP70i was chosen for its advantages over other heat shock proteins. For example, unlike other heat shock proteins, HSP70i is secreted by living cells, thus its actions occur naturally in vivo. In addition, as compared to other heat shock proteins, HSP70i is more effective at eliciting immune responses.

The following trials were conducted using C57BL/6 wild-type (wild-type) mice, HSP70i knockout (HSP70-1 KO) mice, constitutive HSP70 knockout (HSP70-2 KO) mice, and vitiligo-prone, 78B6.Cg-Thy1a/Cy Tg(TcraTcrb)8Rest/J gp100 T cell receptor transgenic (pmel-1) mice. All mice were six to eight weeks of age when included in experiments, excluding the HSP70-2 KO mice which were eighteen to twenty-four months of age, and all mice were gender matched to wild-type mice. The mice were maintained in facilities approved by institutional IACUC regulations.

Figure 1:
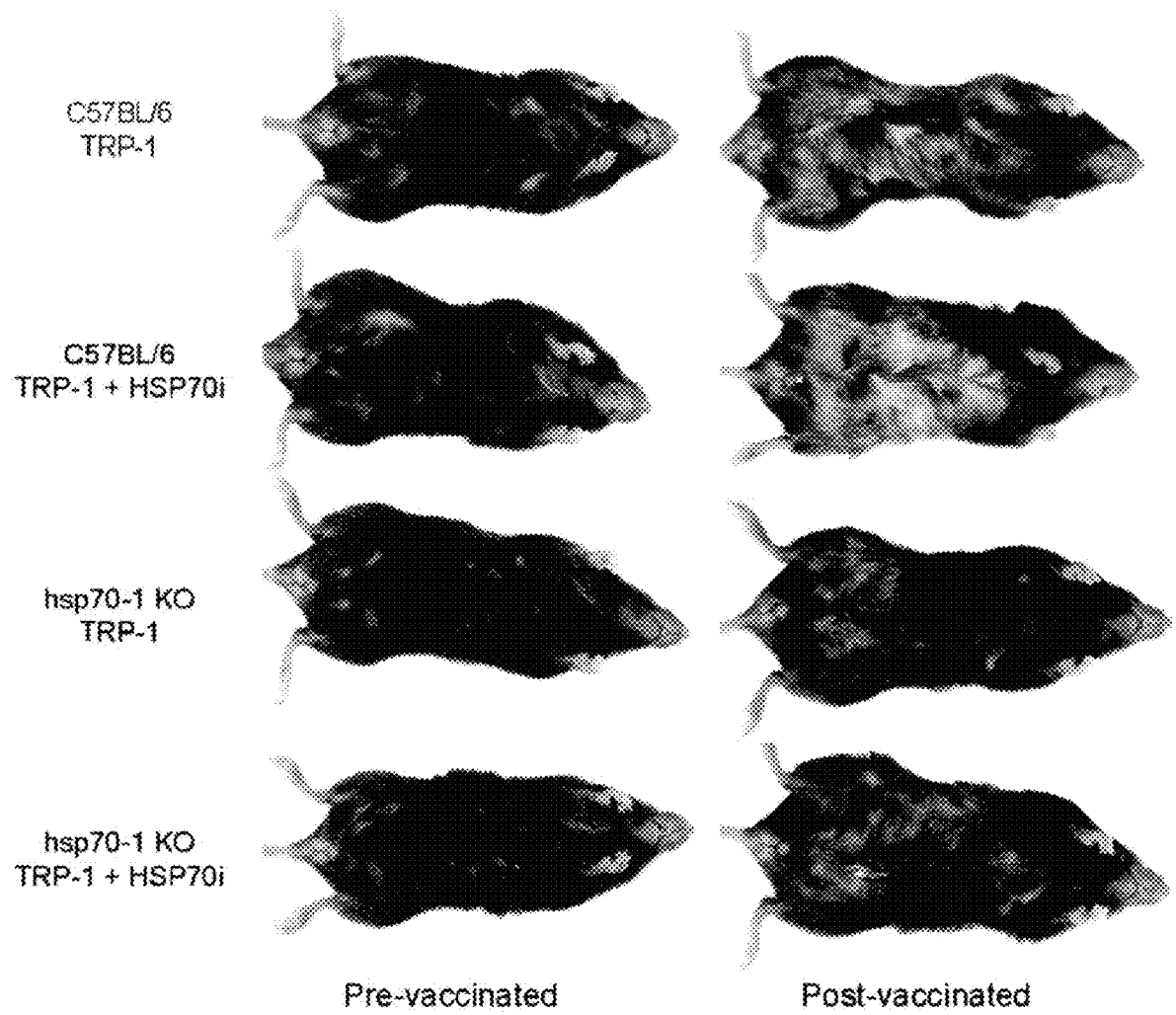
FIG. 1 is a scanned image showing C57BL/6 wild-type (wild-type) mice and inducible heat shock protein 70 knockout (HSP70-1 KO) mice that were gene gun vaccinated with either antigenic Tyrp1ee (TRP-1) or TRP-1 plus inducible heat shock protein 70 (HSP70i) and imaged 4 weeks after the final vaccination.
Figure 2:
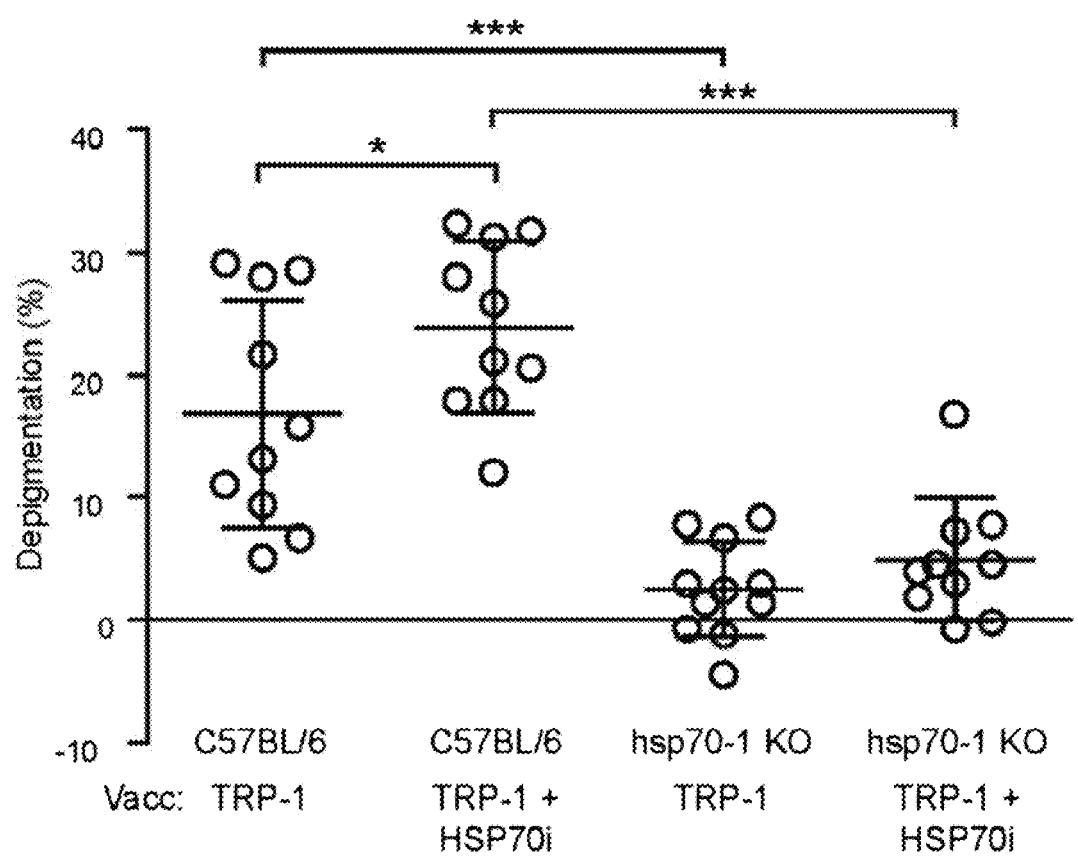
FIG. 2 is a graph representing image analysis of depigmentation in the wild-type mice and the HSP70-1 KO mice of FIG. 1.

A first trial was performed to assess whether there is a sole requirement for HSP70i in mediating depigmentation. Wild-type mice and HSP70-1 KO mice were gene gun vaccinated with antigenic Tyrp1 ee (TRP-1) encoding plasmid. The mice were gene gun vaccinated five times every six days with DNA encoding either six µg of optimized TRP-1 or three µg each of optimized TRP-1 plus HSP70i (SEQ ID NO: 1) and imaged four weeks after the final vaccination. As represented in FIG. 1, depigmentation was virtually absent in the HSP70-1 KO mice. Image analysis confirmed significant depigmentation in the wild-type mice after vaccination with optimized TRP-1, indicating that expression of HSP70i is required for efficient induction of autoimmunity, as represented in the chart of FIG. 2. These results demonstrated that including the human HSP70i encoding plasmid in the vaccine is insufficient to restore the depigmentation process in the HSP70-1 KO mice. Therefore, it is believed that depigmentation is the result of HSP70i-enhanced DC function, accompanied by activation of T cells specifically reactive with melanocytes.

Figure 3A:
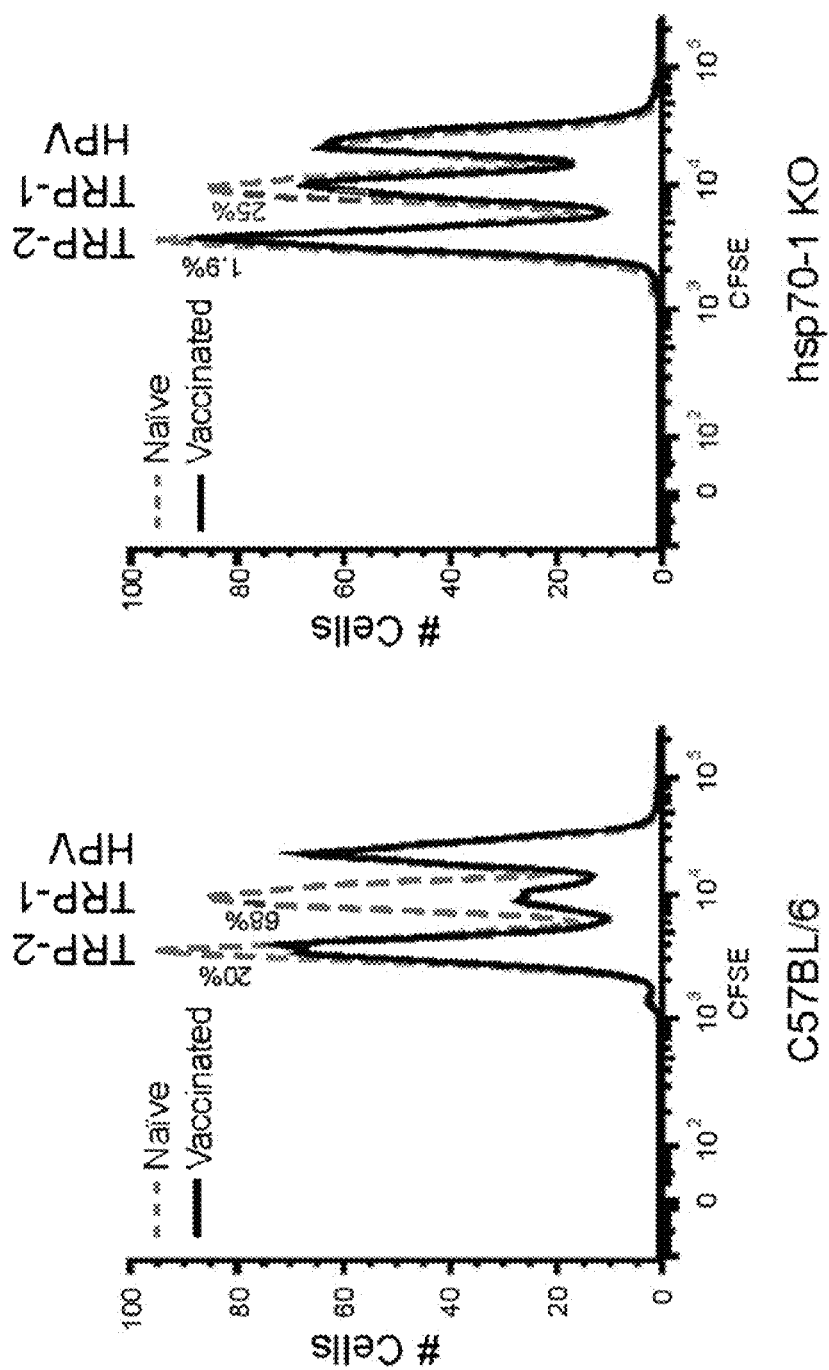
FIG. 3A is a pair of graphs represent fluorescence-activated cell sorting (FACS) used to determine peptide-specific cytotoxic T lymphocyte (CTL) activity for in vivo cytotoxicity assays.
Figure 3B:
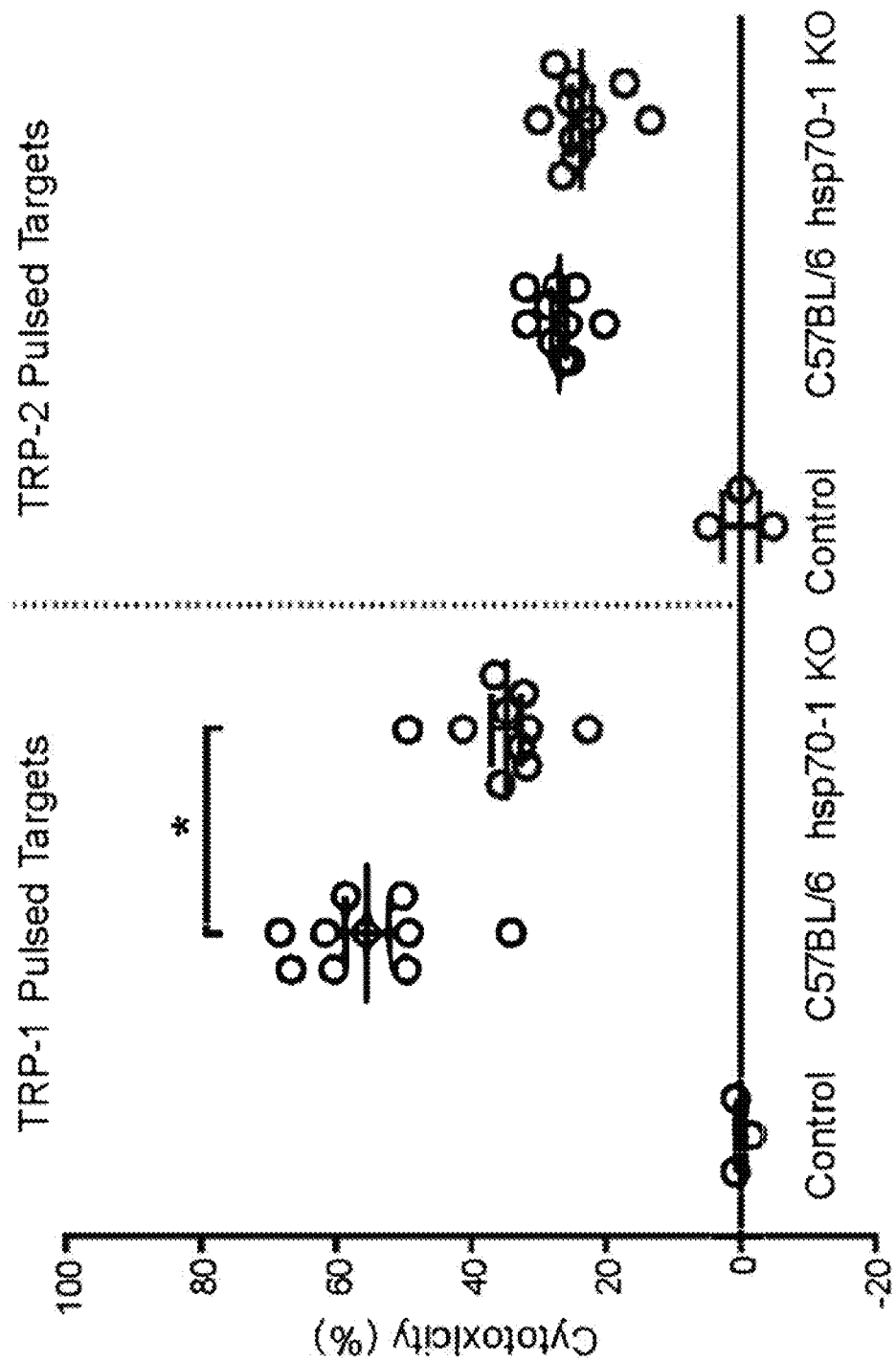
FIG. 3B is a graph representing cytotoxicity in the mice of FIG. 3A.

To determine if HSP70i (SEQ ID NO: 1) mediates the immune activation of cytotoxic T cells (CTL), wild-type mice and HSP70-1 KO mice vaccinated with a combination of optimized TRP-1 and HSP70i encoding plasmids were assessed for in vivo cytotoxicity towards the encoded antigen as well as reactivity towards tyrosinase-related protein 2 (TRP-2). For in vivo cytotoxicity assays, the mice were challenged with splenocytes pulsed with either TRP-1, TRP-2, or irrelevant control peptides plus differing concentrations of carboxyfluorescein succinimidyl ester (CFSE). The mice received two booster gene gun vaccinations three days apart. Spleens were harvested 18 hours after challenge, and fluorescence-activated cell sorting (FACS) was used to determine peptide-specific CTL activity. Data from individual wild-type mice and HSP70-1 KO mice are represented in FIGS. 3A and 3B. The wild-type mice displayed significantly increased killing of splenocytes pulsed with a peptide derived from TRP-1 as compared to the HSP70-1 KO mice following gene gun vaccination, that is, the wild-type mice depigmented significantly more as compared to the HSP70-1 KO mice after either vaccination. The data also reveal cytotoxicity towards the TRP-2 peptide-pulsed splenocytes in all groups, indicating that epitope spreading had occurred. A correlation was observed between increased depigmentation and cytotoxicity towards splenocytes, both of which are augmented by HSP70i. In all, data confirm a solid requirement for HSP70i in inducing CTL mediated autoimmune vitiligo and showed that the HSP70-1 mice are resistant to cytotoxic depigmentation after TRP-1 vaccinations.

Figure 4A:
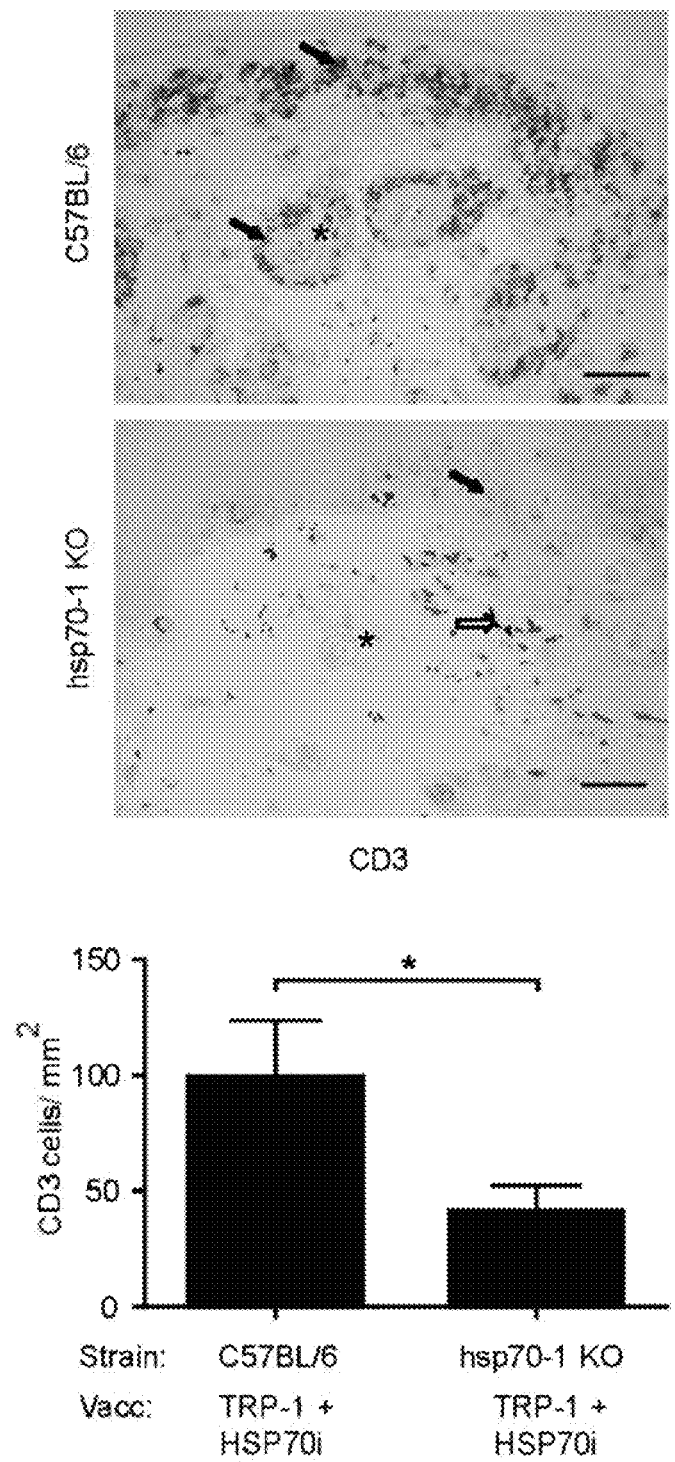
FIGS. 4A and 4B are scanned images showing skin near the dermo-epidermal junction from wild-type mice and HSP70-1 mice one week after a final booster gene gun vaccination and their respective graphs representing quantification of T cell infiltration. CD3+ T cells are represented by solid arrows, hair follicles are represented by asterisks (*) and gold particles are represented by open arrows.
Figure 4B:
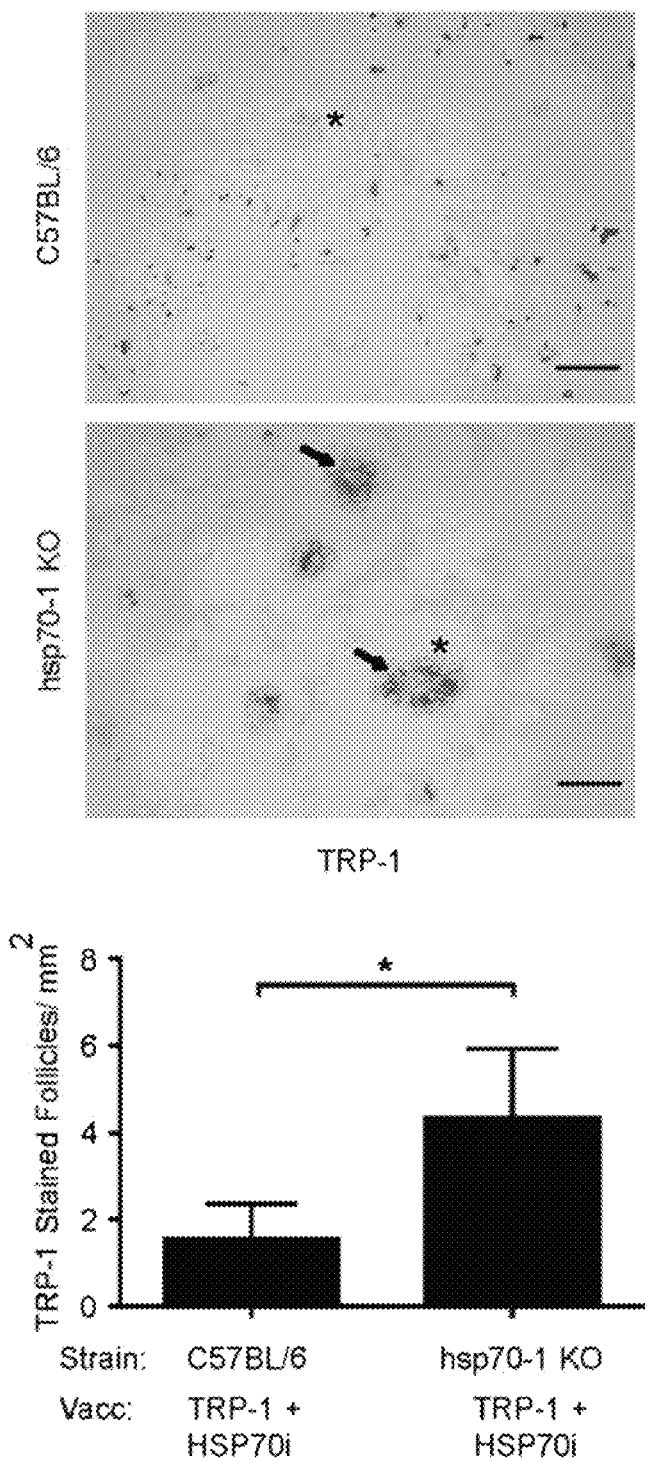

To further support the belief that HSP70-induced skin immune reactivity is responsible for the vitiligo phenotype, local differences in immune reactivity in response to HSP70i (SEQ ID NO: 1) were investigated. Skin from wild-type mice and HSP70-1 KO mice were probed one week following booster gene gun vaccinations using antibodies against the pan T lymphocyte marker CD3 and the density and location of the stained cells was evaluated. FIG. 4A is a scanned image showing skin samples near the dermo-epidermal junction from the wild-type mice containing an increased number of CD3+ T cells (indicated by solid arrows) as compared to the HSP70-1 KO mice one week after a final booster gene gun vaccination. CD3+ T cells are more abundant near hair follicles (indicated by *) in the wild-type mice. Gold particles can also be observed (indicated by open arrow). FIG. 4A further includes a graph representing quantification of T cell infiltration within the skin samples. The vaccinated skin of the wild-type mice contained significantly more T cells than the HSP70-1 KO mice. Consistent with depigmentation data, immunodetection of melanocyte antigen TRP-1 indicated less melanocyte-containing hair follicles were maintained within the wild-type mouse skin as compared to skin from the HSP70-1 KO mice. FIG. 4B is a scanned image showing skin samples with more melanocyte-containing hair follicles in the HSP70-1 KO mice as compared to the wild-type mice after vaccination. TRP-1 expressing melanocytes (indicated by solid arrows) are shown within hair follicles (indicated by *) in the HSP70-1 KO mouse. FIG. 4B further includes a graph representing quantification of melanocyte containing follicles. Depigmentation is shown to correlate with peptide-specific CTL activity, supporting the causative involvement of CD8+ T cells. Taken together, this immunohistology data firmly establish HSP70i induced vitiligo developing in the skin of depigmenting mice indicating that HSP70i is necessary for loss of melanocytes by T cells.

Figure 5A:
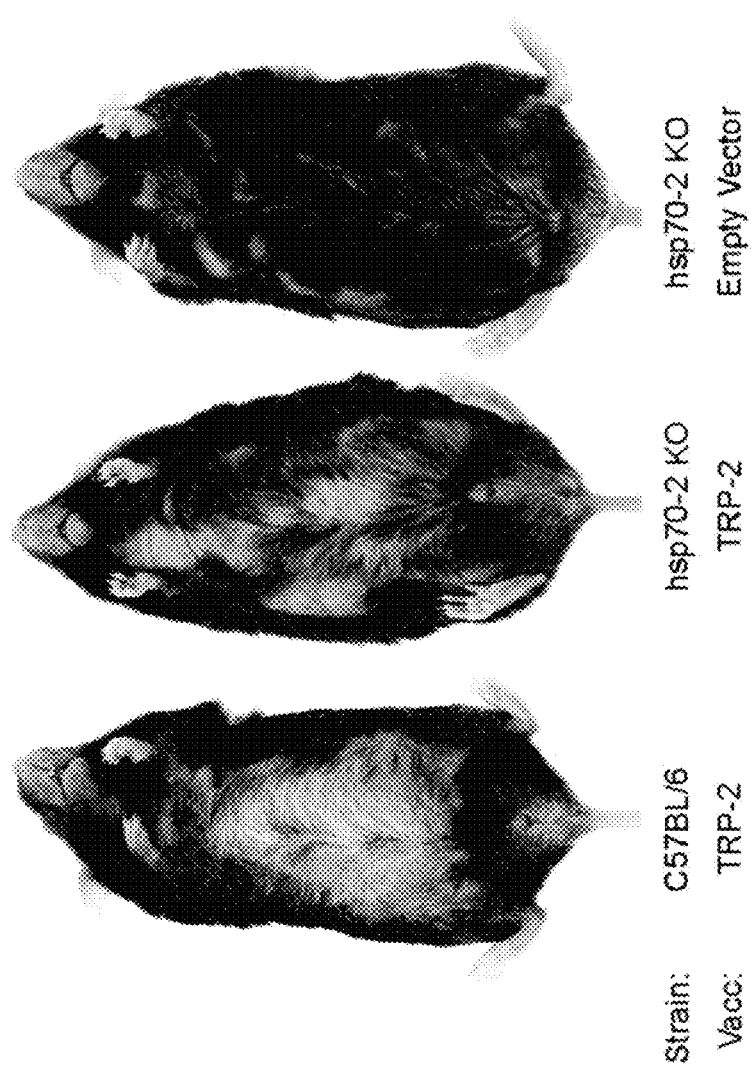
FIG. 5A is a scanned image of wild-type mice and constitutive HSP70 knockout mice (HSP70-2) that were gene-gun vaccinated with either TRP-2 or control DNA (plasmid containing no gene insert).
Figure 5B:
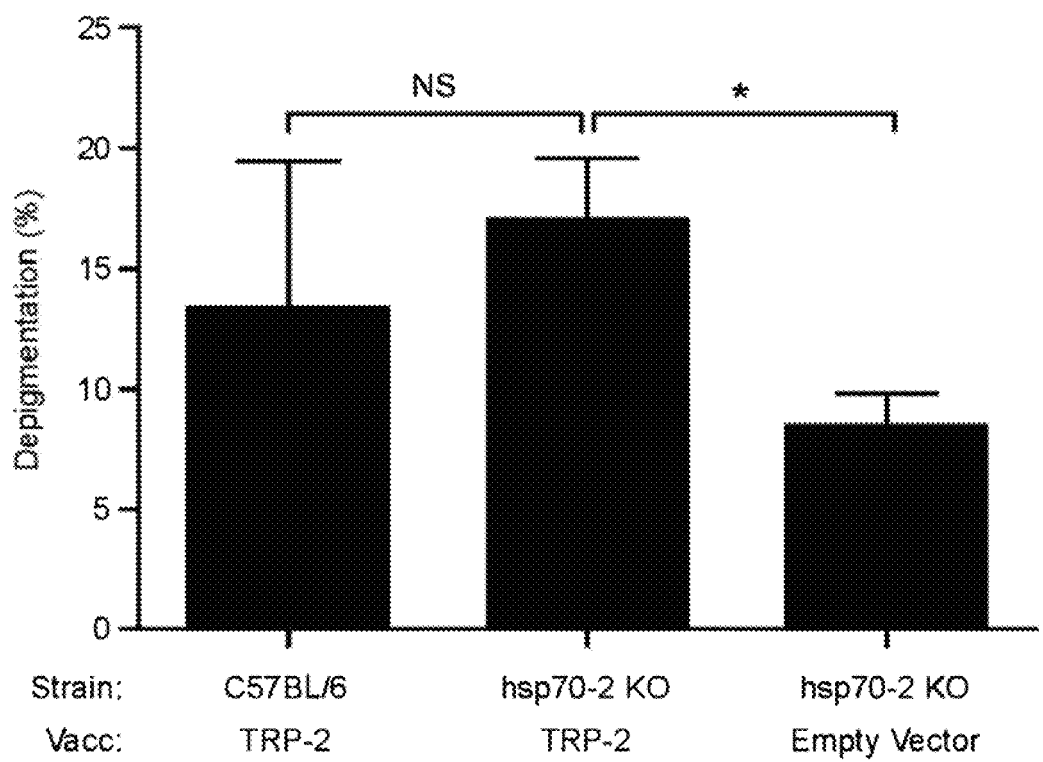
FIGS. 5B and 5C are graphs representing the depigmentation and cytotoxicity, respectively, observed in the mice of FIG. 5A.

In an additional trial, HSP70i (SEQ ID NO: 1) was confirmed to be a sole isoform responsible for accelerating autoimmune depigmentation by gene gun vaccinating HSP70-2 KO mice with TRP-2 encoding plasmid in concentrations sufficient to induce depigmentation in wild-type mice. The wild-type and the HSP70-2 KO mice were gene-gun vaccinated five times every six days with six µg of either TRP-2 or control DNA (plasmid containing no gene insert). FIG. 5A is an image representing depigmentation in the wild-type mice and the HSP70-2 KO mice. Unlike the above trials engaging the HSP70-1 KO mice, no difference in depigmentation was observed between the wild-type and the HSP70-2 KO mice. Conversely, similar amounts of depigmentation were observed in both the wild-type and the HSP70-2 mice vaccinated with TRP-2 as compared to control DNA vaccinations. Visual observations were supported by statistical analysis of quantified data, as represented in the graph of FIG. 5B.

Figure 5C:
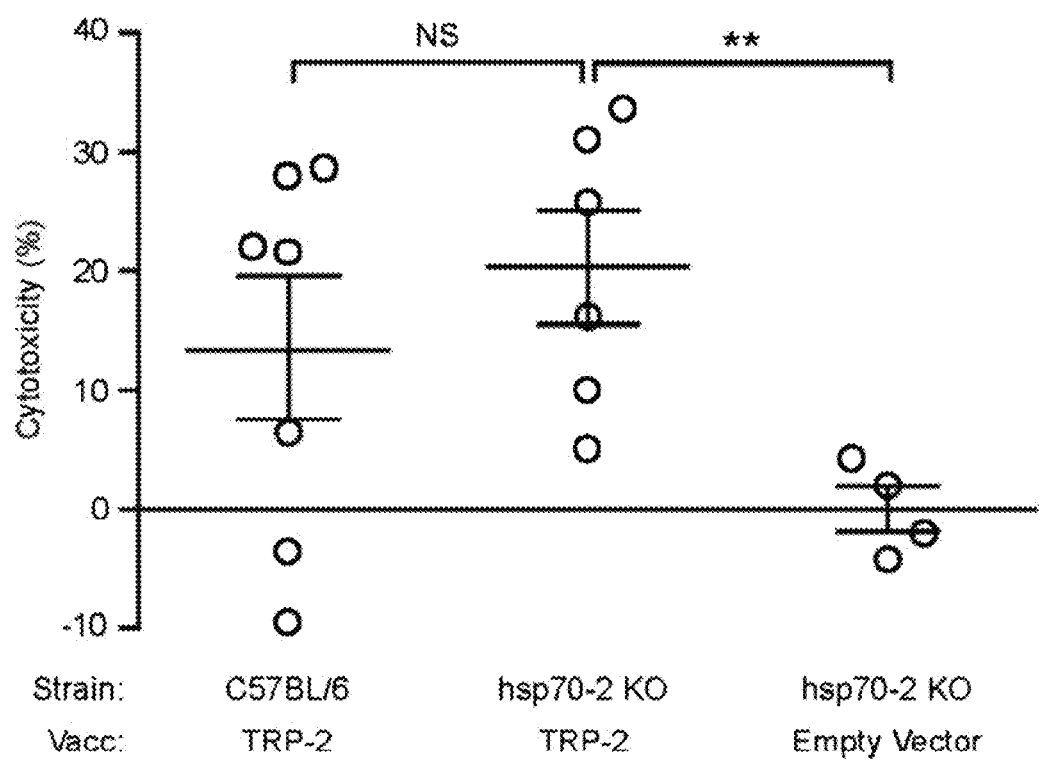

In addition, a graph of FIG. 5C represents that there were no differences in cytotoxicity towards peptide pulsed splenocytes from the wild-type mice and the HSP70-2 KO mice following gene gun vaccination with the TRP-2 encoding plasmid. This is unlike the HSP70-1 KO mice which displayed less killing towards the vaccinated antigen (TRP-1). Together, these data show that constitutive HSP70 is irrelevant for inducing an autoimmune response and further confirm the unique requirement for HSP70i expression in precipitating autoimmune vitiligo.

Due to the results of the above trials, mammalian HSP70i (SEQ ID NO: 1) was investigated to determine if it contains a peptide moiety responsible for binding and activation of DC that may be targeted to modulate autoimmune depigmentation. A database search identified the peptide QPGVLIQVYEGER (residues 435-447 of SEQ ID NO: 5) in human HSP70i as maximally homologous with a DC binding region of microbial HSP70. To assess whether this region is indeed crucial for the autoimmune activation, mutations were inserted via site directed mutagenesis, results of which are represented in a Western Blot of FIG. 6A.

For site directed mutagenesis human and microbial inducible HSP70 were aligned in a BLAST search to identify a 13 amino acid stretch that was maximally homologous to the microbial DC peptide as the putative DC binding domain within human HSP70. Vectors were created with single or double mutations in the putative DC binding region of human HSP70i (HSP70i435-447) using appropriate primers to induce mutations in a sequence QPGVLIQVYEGER (residues 435-447 of SEQ ID NO: 5). As a template for the site directed mutagenesis, an expression vector encoding HSP70i was used as described. In vitro mutagenesis of HSP70 residues was performed on double-stranded template using polymerase chain reaction as previously described. Mutant sequences were verified by DNA sequencing. To verify protein expression, COS7 (CV-1 (simian) in origin, and carrying SV40 genetic material) cells were transfected with individual plasmids encoding human HSP70i, or the mutant HSP70i plasmids using lipofectamine and verified protein expression by Western blotting. Blots were probed with anti-HSP70 Ab (rabbit polyclonal Ab SPA-811 or mouse mAb SPA-810) and alkaline phosphatase-conjugated secondary Abs (goat anti-rabbit, or goat anti-mouse).

Figure 6A:
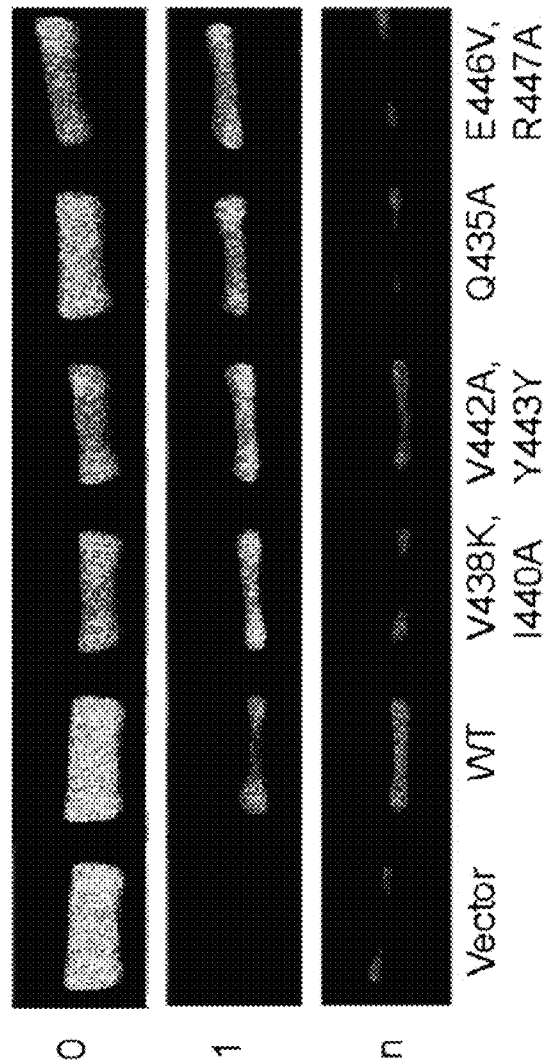
FIG. 6A is a Western Blot representing HSP70i protein expression and antibody recognition.

A mutant plasmid HSP70i(Q435A) (SEQ ID NO: 2) is recognized equally efficiently as wild-type HSP70i (SEQ ID NO: 1) whereas monoclonal antibody SPA-810 shows 20-30% reduced reactivity towards the mutant HSP70i plasmids HSP70i(V438K,I440A) (SEQ ID NO: 4), HSP70i (V442A,Y443V) (SEQ ID NO: 3), and HSP70i(E446V,R447A), as calculated by comparing band intensities for those observed using antibody SPA-811. Thus PGVLIQVYEGER (residues 436-447 of SEQ ID NO: 5) is part of the SPA-810 binding epitope. The resulting plasmids were introduced into COS7 cells to confirm functional protein expression. To identify HSP70i expression, monoclonal antibody SPA-810 generated against a 67-mer peptide partially overlapping with the peptide of interest, and polyclonal antibody SPA-811 which recognizes a C-terminal peptide within HSP70i downstream of a peptide of interest was used. Some expression of HSP70i was observed in COS7 cells as a consequence of the transfection process as indicated by SPA-810 and SPA-811 staining in lanes representing cells transfected with control DNA (vector), as represented in FIG. 6A. Of interest, antibody SPA-810 demonstrated reduced reactivity towards mutants HSP70i (V438K,I440A) (SEQ ID NO: 4), HSP70i(V442A,Y443V) (SEQ ID NO: 3), and HSP70i(E446V,R447A), with resulting staining similar to that of endogenous HSP70i. However, there were no differences in reactivity to mutant HSP70i (Q435A) (SEQ ID NO: 2). Together, these data demonstrate that the HSP70i sequence PGVLIQVYEGER (residues 436-447 of SEQ ID NO: 5) is part of an epitope recognized by SPA-810.

Figure 6B:
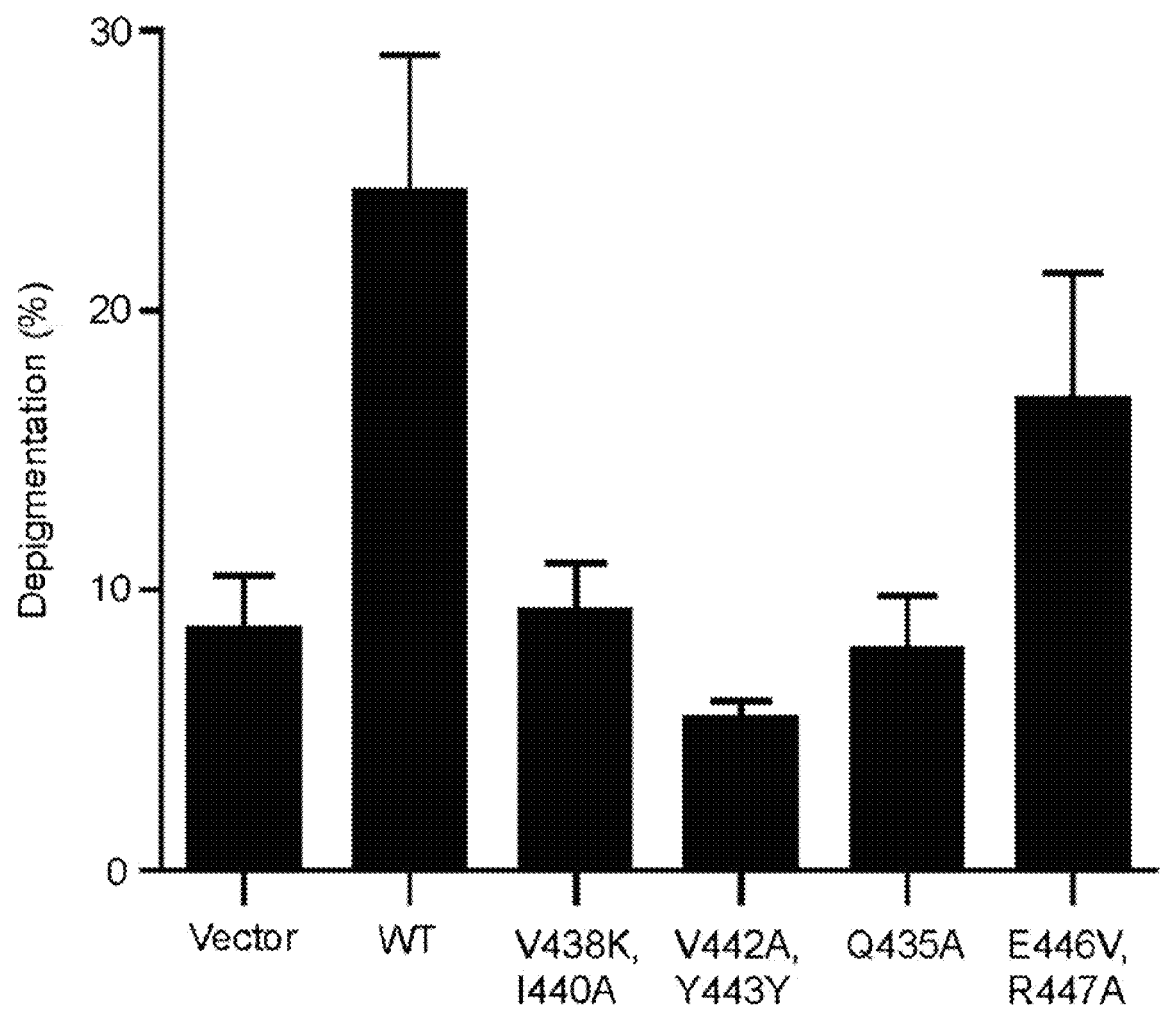
FIG. 6B is a graph representing image analysis of depigmentation in mice vaccinated with mutant versions of HSP70i (including SEQ ID NO: 1) and TRP-2 as compared to wild-type HSP70i.

Depigmenting effects of mutant HSP70i were next investigated in vivo. Wild-type mice were gene gun vaccinated with wild-type or mutant HSP70i and/or TRP-2 encoding plasmids, and assessed for depigmentation. Results of these trials are represented in a graph of FIG. 6B. Image analysis indicated depigmentation is halted in mice receiving vaccinations with mutant versions of HSP70i and TRP-2 as compared to wild-type HSP70i. As represented in FIG. 6B, depigmentation was significantly decreased in the presence of variant sequences HSP70i(V438K,I440A) (SEQ ID NO: 8), HSP70i(V442A,Y443V) (SEQ ID NO: 7), and HSP70i (Q435A) (SEQ ID NO: 6) as compared to unadulterated HSP70i (SEQ ID NO: 5) or HSP70i(E446V,R447A). This indicates that a single amino acid difference in the target peptide region is sufficient to inactivate the depigmentation accelerating effects of HSP70i and supports the crucial involvement of the QPGVLIQVYEG moiety (residues 435-445 of SEQ ID NO: 5) in inducing autoimmune depigmentation.

Figure 7:
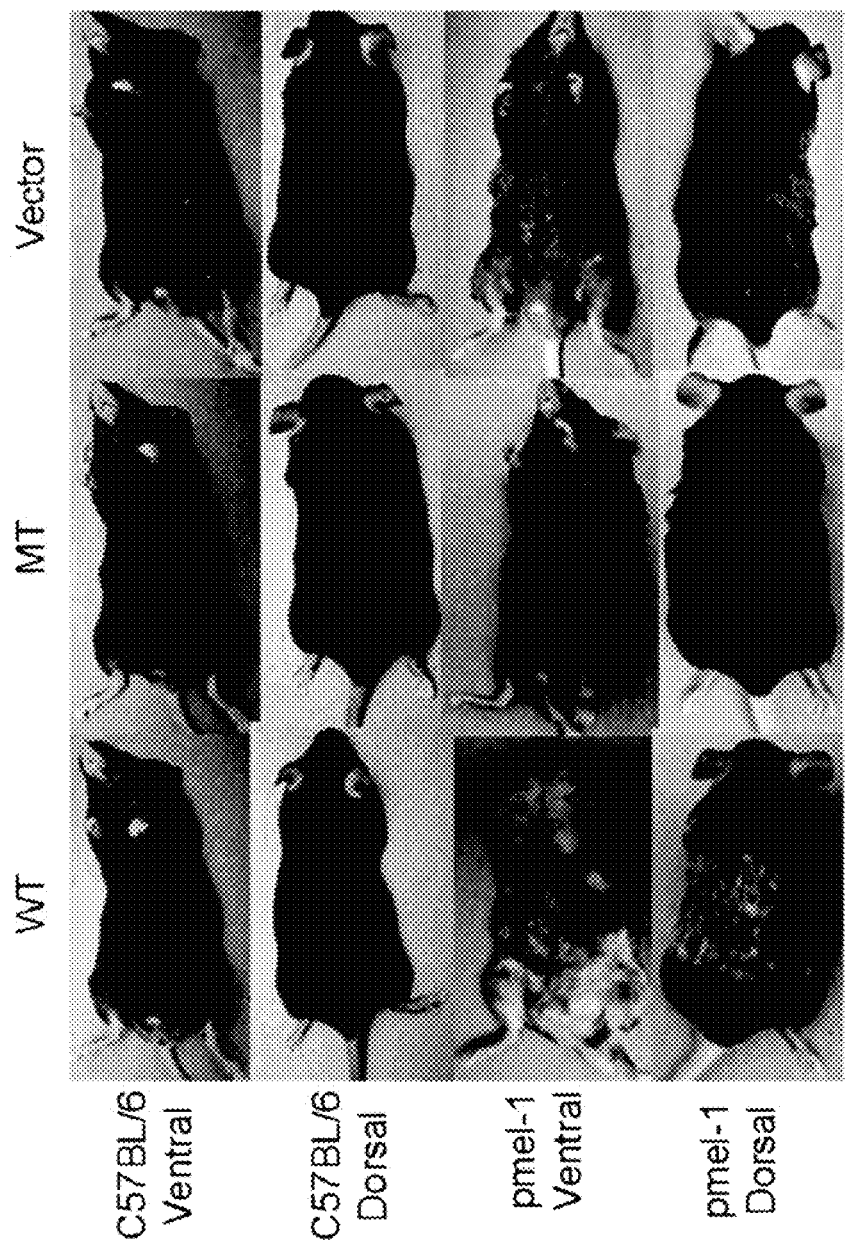
FIG. 7 is a scanned image of wild-type and vitiligo-prone, 78B6.Cg-Thy1a/Cy Tg(TcraTcrb)8Rest/J gp100 T cell receptor transgenic (pmel-1) mice that were vaccinated with either wild-type (WT), HSP70i(Q435A) (MT) (SEQ ID NO: 1), or control DNA (vector) three months after the final gene gun vaccination.
Figure 8:
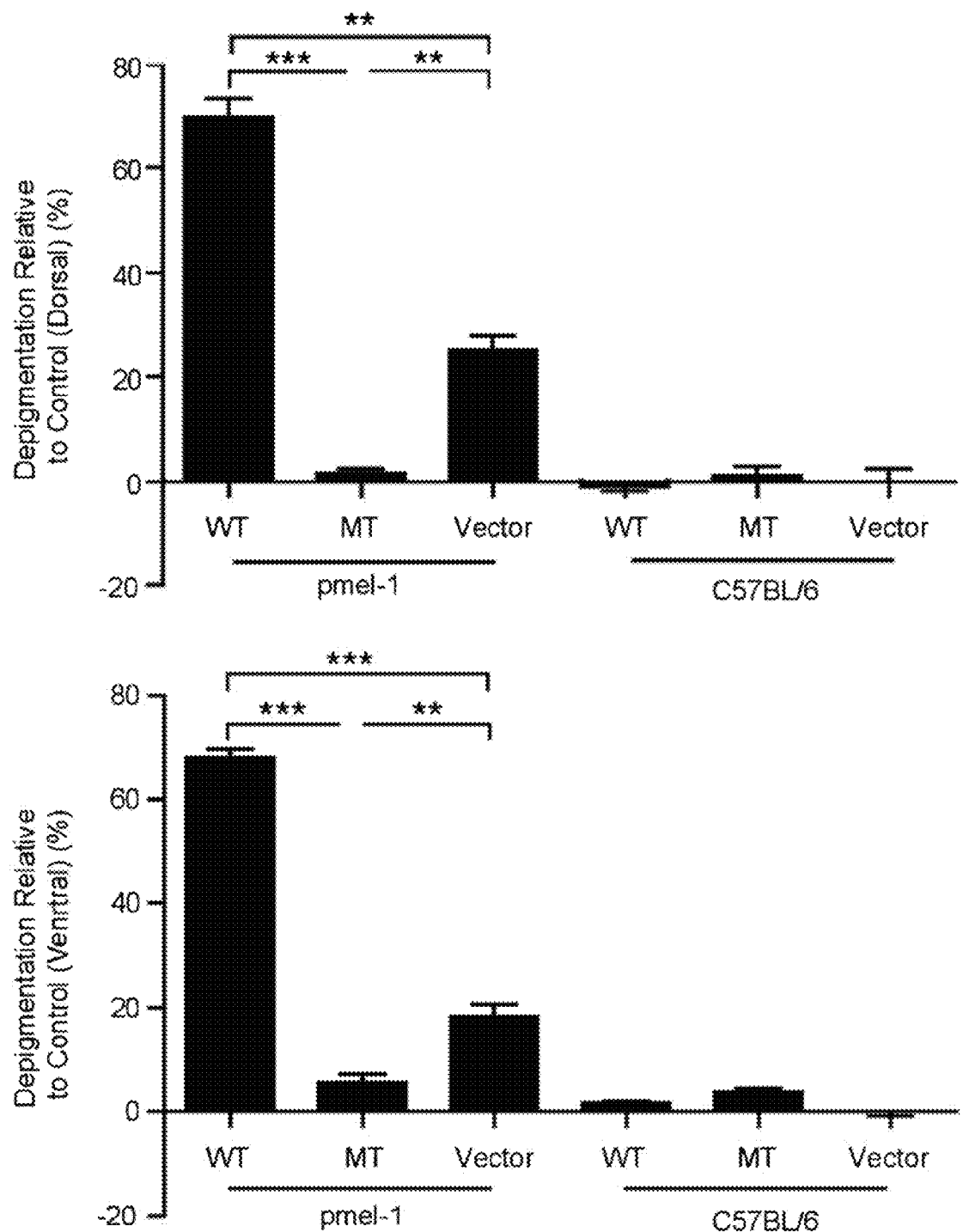
FIG. 8 is a pair of graphs representing quantification of depigmentation of the mice of FIG. 7 relative to control DNA.
Figure 16:
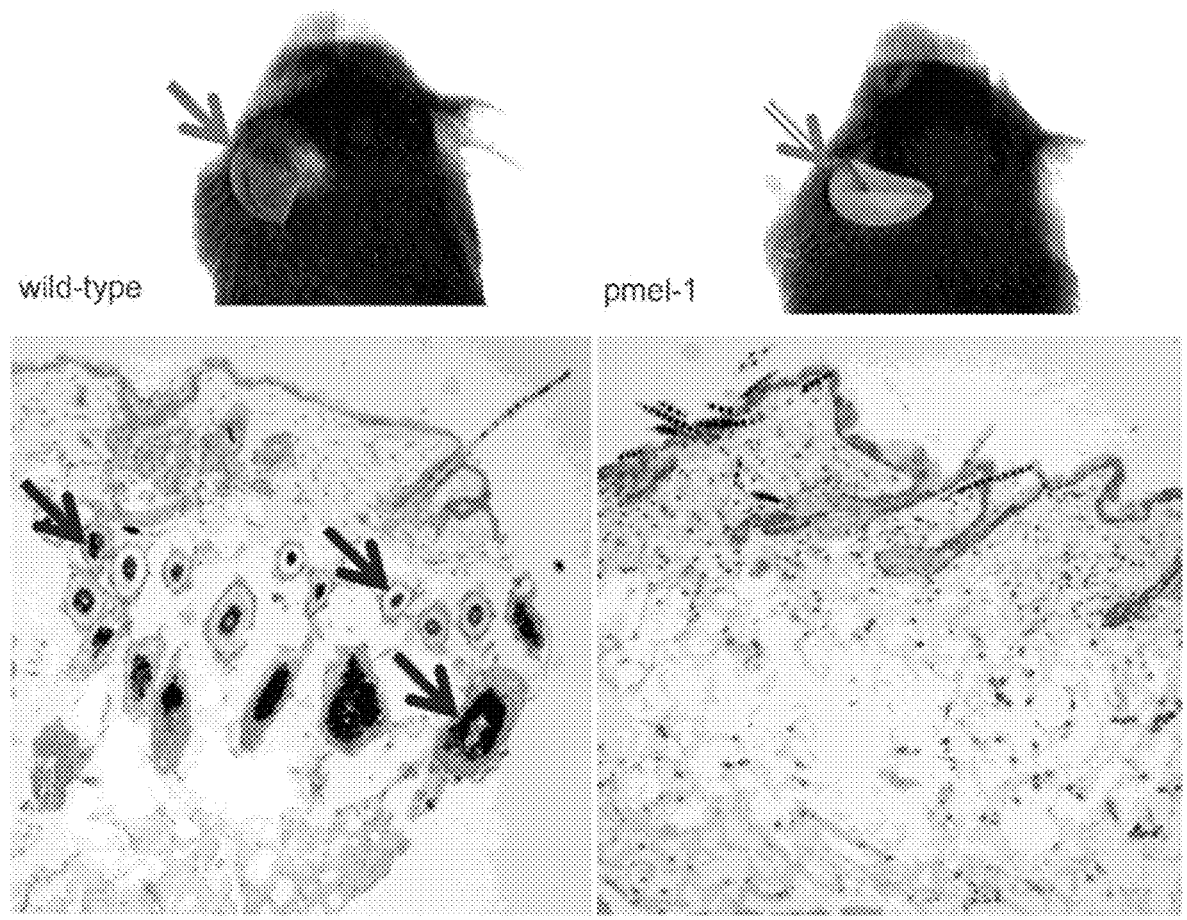
FIG. 16 is a scanned image of a wild-type mouse and a pmel-1 mouse and their respective skin samples prior to testing.

Next, a trial was performed to determine whether HSP70i (SEQ ID NO: 5) alone is sufficient to establish depigmentation in animals predisposed to developing autoimmune depigmentation, akin to human vitiligo. Pmel-1 mice and wild-type mice were gene gun vaccinated with wild-type HSP70i (SEQ ID NO: 1) and mutant HSP70i(Q435A) (SEQ ID NO: 2) plasmids, as well as control DNA. The wild-type and the pmel-1 mice were vaccinated three times every seven days with four µg of either wild-type (WT; SEQ ID NO: 1), HSP70i(Q435A) (MT; SEQ ID NO: 2), or control DNA (vector). Three months after the final vaccination, the pmel-1 mice vaccinated with wild-type HSP70i displayed significantly increased ventral and dorsal depigmentation compared to mutant HSP70i or control DNA, as represented in FIG. 7. Graphs of FIG. 8 represent that upon quantification, the pmel-1 mice receiving wild-type HSP70i-encoding DNA displayed significantly more depigmentation as compared to control DNA vaccinations and wild-type HSP70i, confirming that focal overexpression of HSP70i is sufficient to induce vitiligo in disease-prone mice. As expected, no depigmentation was observed in the wild-type mice gene gun vaccinated with any plasmid. Importantly, ventral and dorsal depigmentation was significantly decreased in the pmel-1 mice gene gun vaccinated with mutant HSP70i (Q435A) (SEQ ID NO: 2) plasmid as compared to the pmel-1 mice vaccinated with control DNA. FIG. 16 is a scanned image of a wild-type mouse and a pmel-1 mouse and their respective skin samples prior to testing. As shown in FIG. 16, the pmel-1 mouse has already lost its differentiated melanocytes prior to testing. This indicates that a single missense nucleotide variation in HSP70i derivative peptide region is sufficient not only to abrogate the vitiligo-inducing effect of natural HSP70i, but also to actively interfere with immune activation and subsequent depigmentation.

Figure 9A:
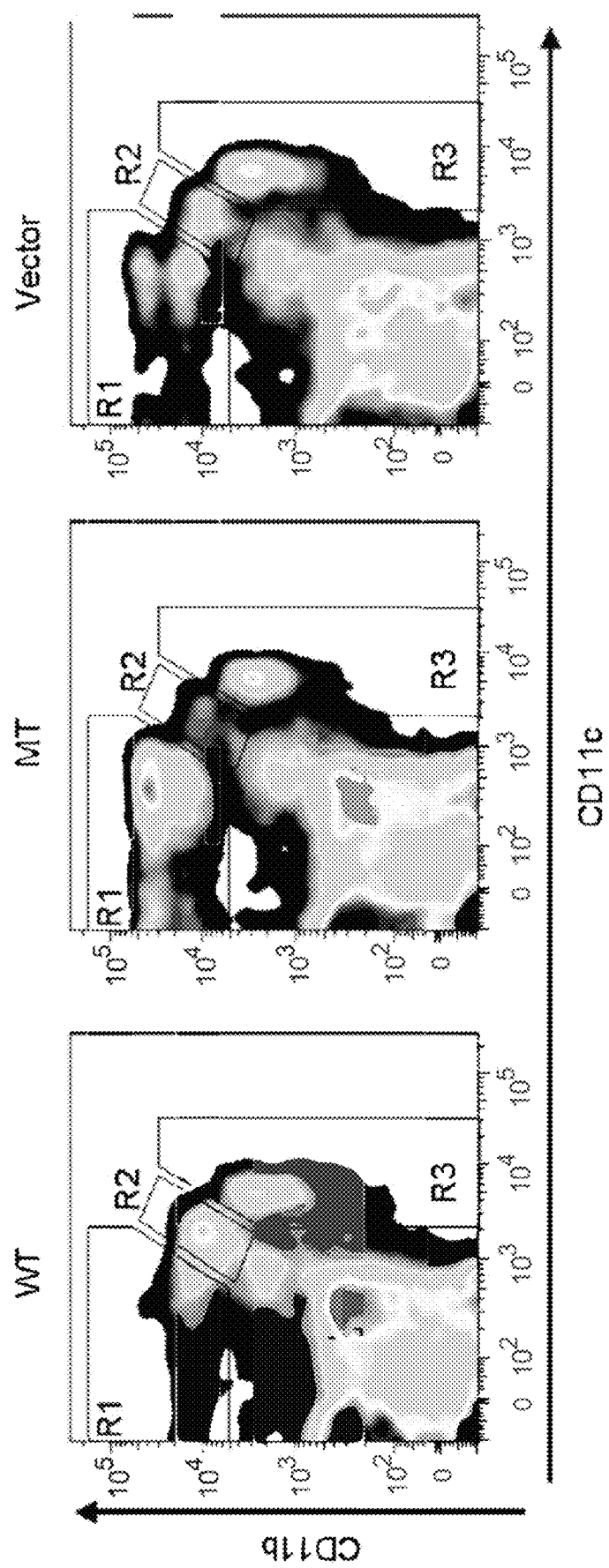
FIGS. 9A and 9B are graphs representing quantification of splenocytes obtained from pmel-1 mice nine months after gene gun vaccination with wild-type (WT; SEQ ID NO: 1) or mutant HSP70iQ435A (MT; SEQ ID NO: 2), and control DNA (vector) and were stained to discriminate leukocyte subpopulations, and staining was quantified by flow cytometry.
Figure 9B:
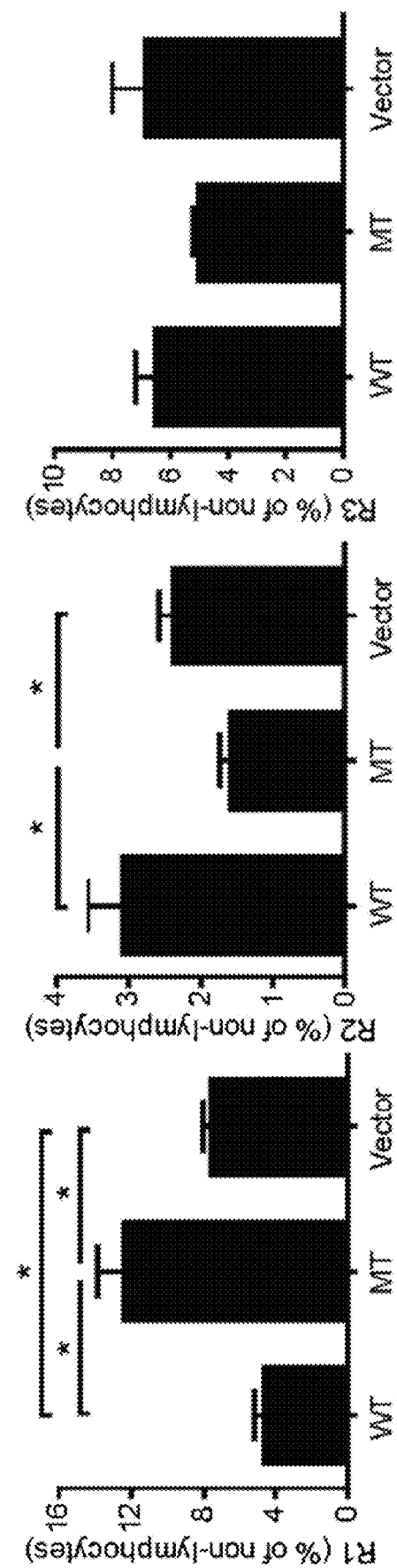

As the QPGVLIQVYEG moiety (residues 435-445 of SEQ ID NO: 5) proved crucial to the depigmentation process, its role in DC activation was further analyzed by FACS analysis. DC profiles were obtained from splenocytes of mice euthanized nine months after vaccination. The mouse splenocytes were stained for lymphocyte markers CD3, CD8, and IgM-Thy1.2, non-lymphocyte markers CD11b, CD11c, and F4/80, as well as DC maturation markers CD80, CD86, and MHC II. Stained cells were then followed by flow cytometry to delineate cell populations and their state of activation. For trials including pmel-1 knockout mice, splenocytes were recovered twenty-five weeks after the final vaccination, and immediately stained. Initial gating was performed on live non-debris singlets, with subsequent gating towards CD11c versus CD11b cells using FACS canto equipment. Thy1.2-IgM, and CD3 positive cells were excluded from the final gating. Notably, marked differences were observed in the abundance of monocyte-derived subpopulations discriminated based on CD11b and CD11c expression levels, shown as R1 through R3 in graphs represented in FIG. 9A. Three distinct populations of cells were observed after gating for CD11b and CD11c cells in the non-lymphocyte population, with high (hi), low (lo) or intermediate (int) levels of expression. Macrophages are observed in the R1 population as CD11bint/hiCD11clo, while DCs are amongst the R2 and R3 populations as CD11bintCD11cint and CD11bloCD11chi respectively. The R3 conventional DC population remained unchanged, yet monocyte derivative populations were markedly biased towards CD11b expression within mice vaccinated with DNA encoding mutant HSP70i when compared to wild-type HSP70i encoding or control DNA. Graphs in FIG. 9B represent quantification of CD11b and CD11c expressing cells determined differential expression of these markers among leukocytes after vaccination with wild-type (SEQ ID NO: 1) or mutant HSP70i(Q435A) (SEQ ID NO: 2) plasmids. Intriguingly, the population R1 was increased by the mutant HSP70i(Q435A) (SEQ ID NO: 2) vaccination, whereas the same population is suppressed after vaccination with wild-type HSP70i (SEQ ID NO: 1). The DC population R2 (CD11bintCD11cint) representative of pro-inflammatory DCs shows an opposite trend. These data demonstrate that HSP70i can drive the relative abundance of immune cell subpopulations associated with autoimmune depigmentation. The QPGVLIQVYEG moiety (residues 435-445 of SEQ ID NO: 5) is involved in depigmentation by defining the prevalence of dendritic cell subsets important for CTL activation, and mutations in this region alter the macrophage and DC ratios.

After determining that mutant HSP70i can halt disease in vitiligo-prone mice, trials were performed to investigate potential side effects. Specifically, when inhibiting autoimmunity, there is also a concern of inhibiting immunity in general and patients may not be able to mount an anti-tumor response. Therefore, wild-type and CD8 knockout mice were gene gun vaccinated first with autoimmune treatments as described above and then gene gun vaccinated with tumors.

Figure 10:
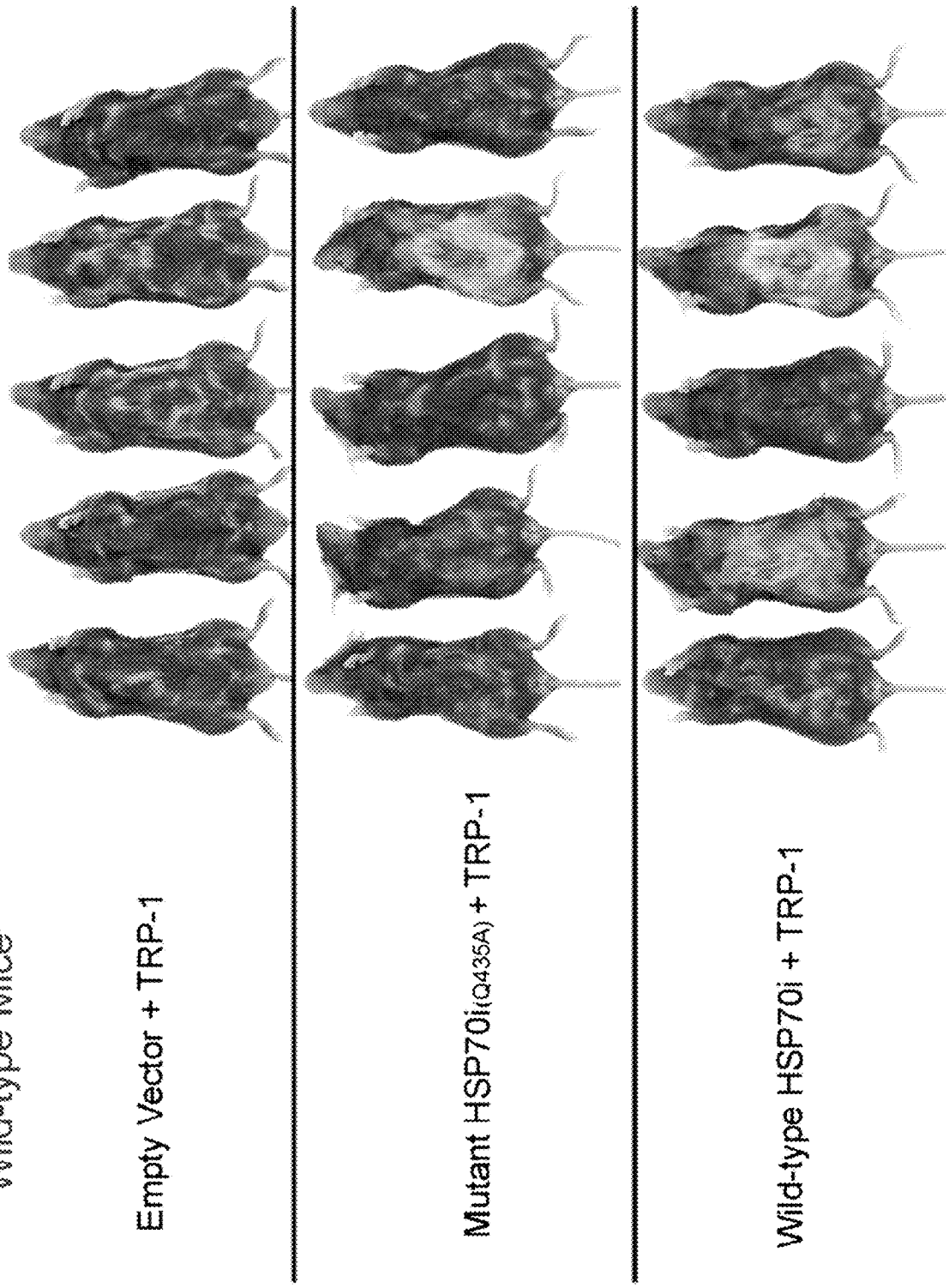
FIGS. 10 and 11 are scanned images representing wild-type mice and CD8 knockout mice that were vaccinated with either control DNA and TRP-1, HSP70i(Q435A) (SEQ ID NO: 2) and TRP-1, or wild-type HSP70i (SEQ ID NO: 1) and TRP-1.
Figure 11:
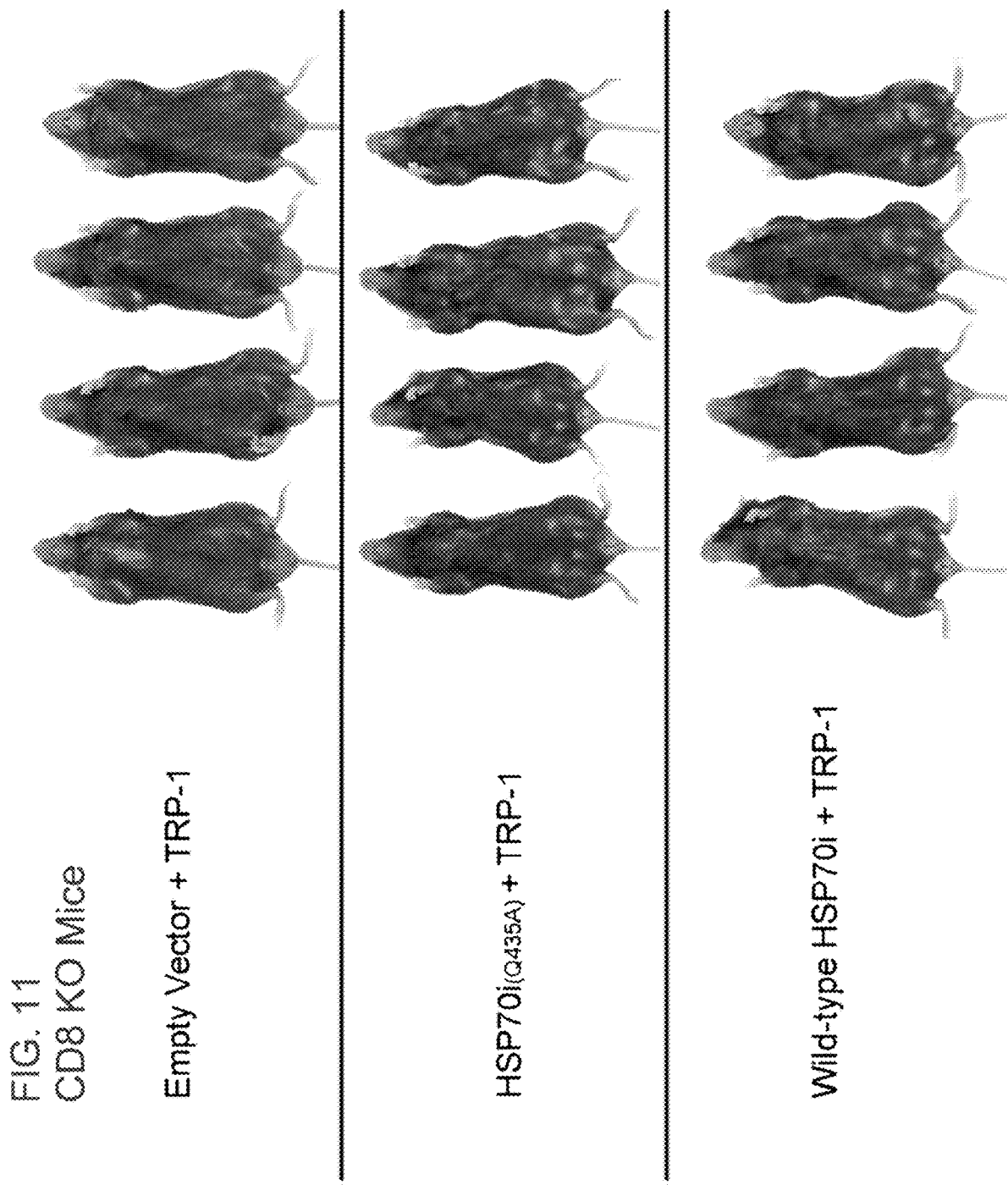
Figure 12:
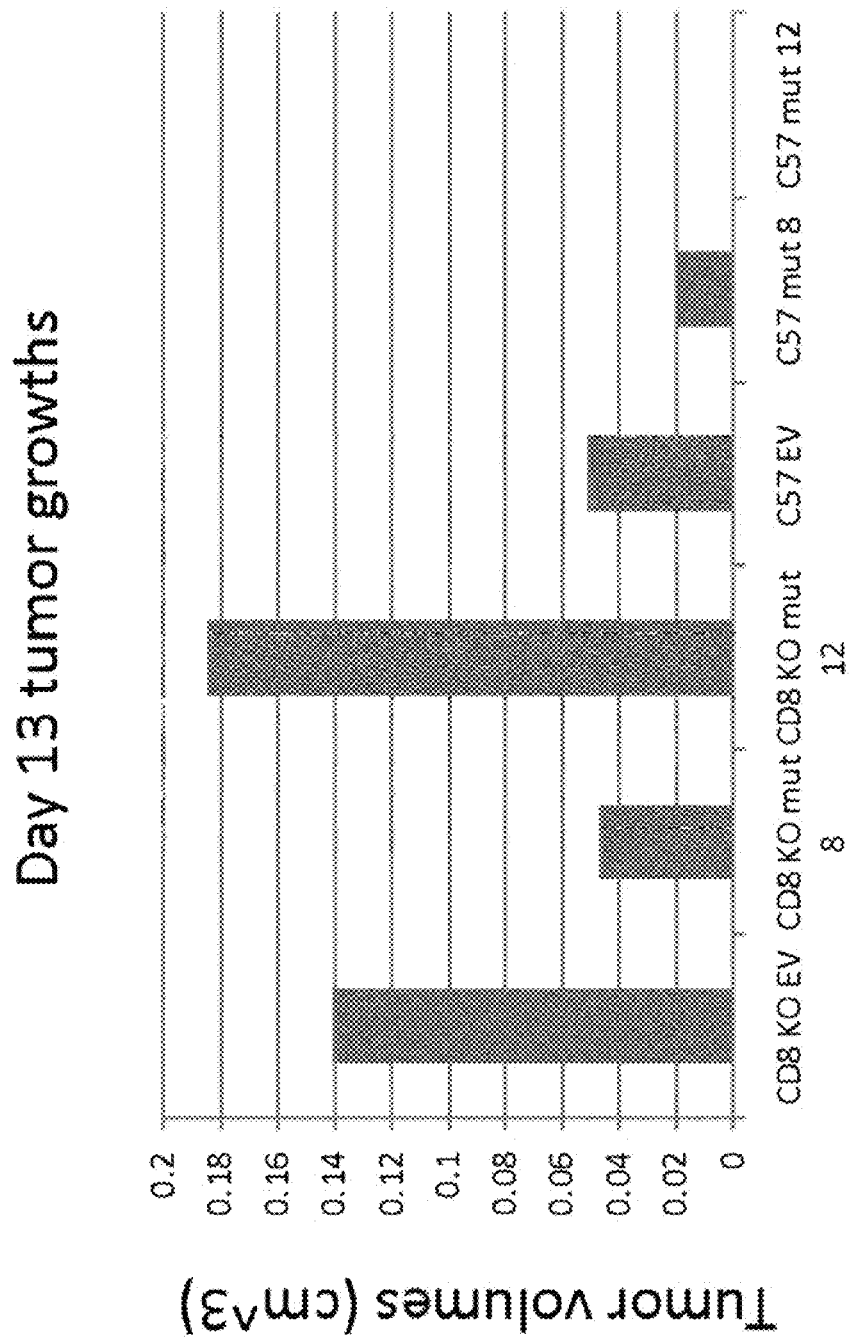
FIGS. 12 and 13 are graphs representing observed tumor growth in the mice of FIGS. 10 and 11.
Figure 13:
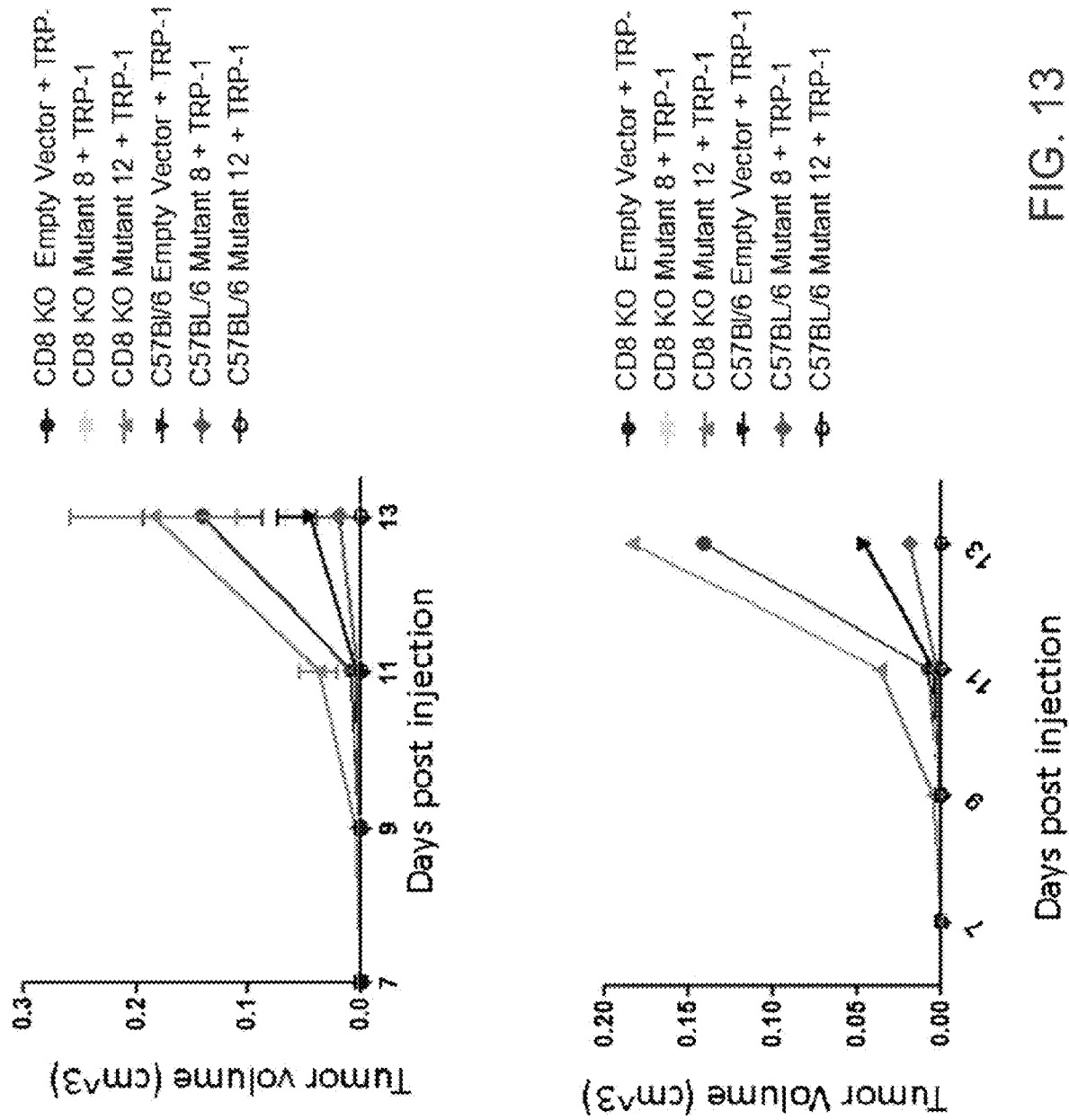
Figure 14:
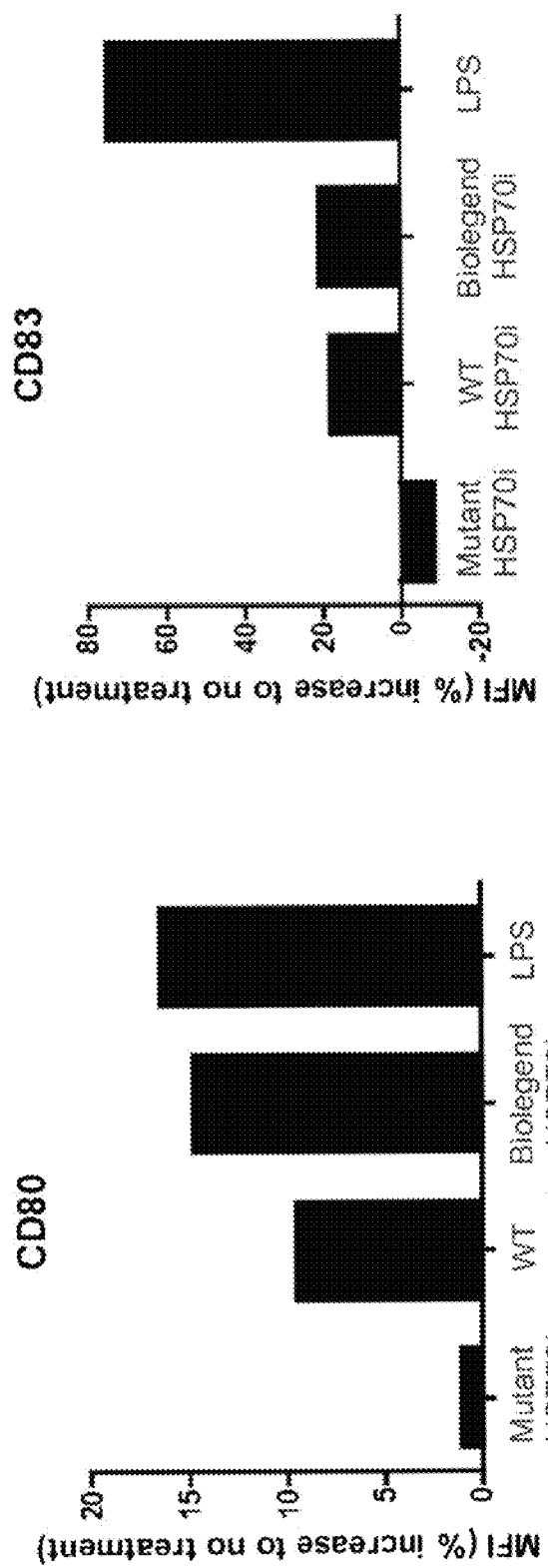
FIGS. 14 and 15 are graphs representing quantification of monocytes harvested and magnetically sorted from peripheral blood of the mice of FIGS. 10 and 11 and stained for CD11C, CD80, CD86, CD83, HLA-DR, HLA-DR, all directly with conjugated fluorochromes.
Figure 15:
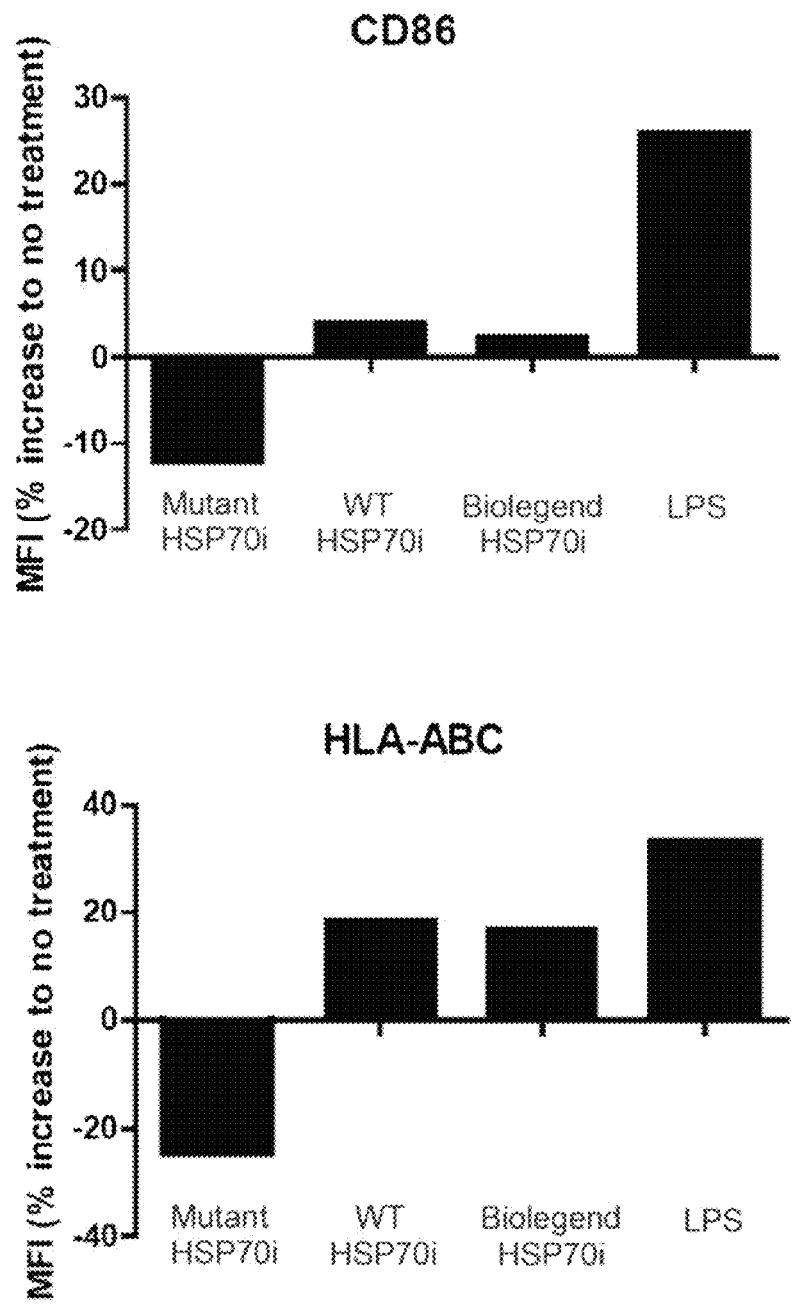

Wild-type and CD8 KO mice were vaccinated with control DNA and TRP-1, Wild-type HSP70i (SEQ ID NO: 1) and TRP-1, or mutant HSP70i(Q435A) (SEQ ID NO: 2) and TRP-1. The wild-type and CD8 KO mice were given a dosage of three µg of each plasmid for a total of six µg each and were vaccinated five times, six days apart. FIGS. B1 and B2 are images showing the wild-type and CD8 KO mice six weeks after final vaccination when they were assessed for depigmentation. Thereafter, the wild-type and CD8 KO mice were injected with two booster vaccinations of 100,000 B16F2 cells, five days apart. FIGS. 10 and 11 are graphs representing the observed tumor growth in the wild-type and CD8 KO mice.

To determine DC stimulation within the wild-type and CD8 KO mice, monocytes were harvested and magnetically sorted from peripheral blood. 250,000 cells were added to five milliliters of media (RPMI, 10% FBS, Pen/strep) in teflon containers. GM-CSF and IL-4 were added to drive DC differentiation and half of the media was changed every other day. On day 6, one ug/ul of either His tag sorted wild-type (SEQ ID NO: 1) or mutant HSP70i(Q435A) (SEQ ID NO: 2), commercially available HSP70i, LPS, or nothing was added. On day 7, the cells were stained for CD11C, CD80, CD86, CD83, HLA-DR, and/or HLA-DR all directly with conjugated fluorochromes. FACS analysis gating on DC population was performed (measured by forward and side scatter, and CD11C positivity). The results of the trial are represented in graphs of FIGS. 12, 13, 14, and 15. These results reveal that animals treated with mutant HSP70i (SEQ ID NO: 2) are still protected from tumors compared to animals treated with wild-type HSP70i (SEQ ID NO: 1).

More recently, trials have been performed to understand the differential effects of wildtype HSP70i and mutant HSP70i on DC activation by studying enhanced expression of activation markers in response to either isoform. It is believed that the natural variant activates DC in vitro while the mutant HSP70i does not.

In the above trials, the exclusive, causative role of HSP70i in inducing autoimmune depigmentation in mice was examined. Using constitutive and inducible HSP70 knockout mouse models, it was determined that the inducible, but not constitutive isoform of HSP70 is solely responsible for inducing and perpetuating an autoimmune response.

Previous vaccination studies using HSP70 in combination with melanocyte antigens at suboptimal levels have shown that immune responses can be elicited towards cells bearing these target antigens. This specificity is best attributed to the chaperone function of HSP70 in binding these antigens. In addition, these trials showed that depigmentation preferentially occurred after inclusion of HSP70i in the vaccine, demonstrating the importance of this protein in perpetuating and precipitating autoimmune responses.

Importantly, these trials show that injecting mice with a combination of HSP70 and melanocyte antigen encoding plasmids is sufficient for inducing vitiligo, and this response is mediated by CD8+ T cells. These trials demonstrate the shared relationship between vitiligo and melanoma in the targeting of specific cells mediated by HSPs. Here, it was determined that depigmentation in wild-type mice occurred within and distal to the site of the gene gun vaccination, as represented in FIGS. 1, 2, 3A, 3B, 7, and 8. Cytotoxicity towards melanocytes is now believed to be due to an antigen-specific and systemic immune response. Here, the HSP70i KO mice displayed reduced killing of melanocyte antigen pulsed splenocytes, indicating a role for HSP70 in the immunogenicity towards these cells.

In the case of anti-tumor immunity, HSP70i is believed to efficiently chaperone tumor antigens, drive DC activation, or directly activate the adaptive immune system. In the latter, APCs will be activated leading to the recruitment of effector cells, and the eventual killing of target cells. Interestingly, in the above trials both in the wild-type and HSP70i KO mice that were vaccinated with TRP-1 plasmid, killing of TRP-2 pulsed splenocytes was observed indicating that epitope spreading had occurred.

Previous studies have observed that perilesional skin of expanding lesions in vitiligo patients contains greater numbers of T cell infiltrates as compared to control skin. T cell mediated autoimmune responses to melanocytes are accompanied by the presence of melanocyte specific CTLs in vitiligo patient skin. The histological staining of the above trials show that the skin from the wild-type mice had greater numbers of T cells as compared to the HSP70-1 KO mice after vaccinating each with TRP-1, and there was an even greater increase with the addition of HSP70i plasmid (not shown). These observations were inversely related to the loss of melanocytes within the wild-type mice, which can be attributed to increases in self-reactive CTL. Generally, vaccinating with TRP-1 (Tyrp1 ee) elicits highly effective T cell responses; however, it was showed that in the absence of endogenous HSP70i, T cell tolerance towards melanocytes is maintained. On the other hand, removing constitutive HSP70 still resulted in melanocyte death. This confirms that only HSP70i is required to elicit an autoimmune response.

Extracellular HSP70 has been shown in previous studies to activate DC directly, and via the peptides they chaperone. These studies have shown that the C-terminal portion of HSP70 (residues 359-610) stimulates DC, and supports Th1 polarization, driving cytokine production of TNF-a, IL-12, and release of NO release. Therefore, a peptide sequence QPGVLIQVYEG (residues 435-445 of SEQ ID NO: 5) (HSP70434-444) was identified as a potential target for blocking entities to prevent DC activation. From the trials above, the peptide sequence QPGVLIQVYEG (residues 435-445 of SEQ ID NO: 5) was implicated as a novel target in preventing an autoimmune response, and a potential therapy in autoimmune disorders such as vitiligo.

The stand-alone function of HSP70i was evaluated in a spontaneous mouse model of vitiligo to demonstrate its immune enhancing effects. The pmel-1 mice were engineered to have self-reactive T cells expressing a T cell receptor reactive to the melanocyte antigen gp100. These pmel-1 mice faithfully mimic human vitiligo in which melanocyte reactive T cells escape clonal deletion, and stress is shown to augment the T cell response. The p-mel1 mice were vaccinated not only with wild-type HSP70i (SEQ ID NO: 1) to look for accelerated establishment of autoimmune disease, but also with a representative mutant sequence to look for abrogation of the same response. Comparison of FIGS. 7 and 16 show that the mutant HSP70i may be used to reduce the progression of vitiligo but to regain pigmentation of the white skin.

Importantly, it had already been shown that as little as a single residue change in this region is sufficient to fully prevent the depigmentation inducing effects in mice when vaccinated in combination with TRP-2. Vaccination with mutant HSP70i(Q435A) (SEQ ID NO: 2) fully abrogated the gradual depigmentation observed in aging mice or animals vaccinated with the plasmid control DNA. The trials showed that depigmentation is accelerated after vaccination with wild-type HSP70i, again demonstrating the importance of this protein in precipitating disease.

Here, FACS analysis of the pmel-1 mice splenocytes revealed phenotypes of CD11c and CD11b cells as reported in the wild-type mice. Previous studies reported that Treg homing to skin is severely reduced in vitiligo patients, which may in part be associated with a decline of the skin homing chemokine CCL22. Importantly, the above trials demonstrate that the same subset of Treg inducing macrophages is down or upregulated by wild-type and mutant HSP70i (Q435A) (SEQ ID NO: 6), respectively. Thus, wild-type HSP70i (SEQ ID NO: 5) may contribute to vitiligo through the inhibition of Treg via reduced macrophage activity, and through supporting Th17 mediated autoimmunity by inflammatory DC. It is believed then that HSP70i may be acting on two fronts, by activating CTLs via DC activation, and simultaneously downregulating Treg activity. By contrast, HSP70i(Q435A) (SEQ ID NO: 6) drives an opposite, anti-vitiligo phenotype. The differential immune effects of wild-type versus mutant HSP70i are believed to be related to mutations in the DC activating peptide QPGVLIQVYEG (residues 435-445 of SEQ ID NO: 5).

HSP70 has been implicated in previous studies in various autoimmune disorders including diabetes and rheumatoid arthritis. In addition, the release of HSP70i by necrotic cells may augment inflammation such as that seen with acute myocardial infarction (AMI). This renders therapeutic measures that interfere with immune functions of HSP70 of primary importance. Here, the trials showed that HSP70i plays a crucial role in another autoimmune disorder, vitiligo. The data indicate that HSP70i has an important role in inducing depigmentation by activating DC and subsequent breaking of T cell tolerance to self antigens. This implicates HSP70i as a crucial molecule defining a bottleneck in the etiopathology of vitiligo.

Preventing secreted HSP70i from inducing an autoimmune response will prove as an important strategy for treating autoimmune disorders. Currently, treatments for vitiligo typically involve local immune suppression through topical hydrocortisone application, and psoralen plus UVA (PUVA) therapy; however, the success rate is quite limited and involves long lag periods. Several groups have implicated the local production of reactive oxygen species (ROS) in vitiligo as well as other autoimmune disorders. Therefore, it has been proposed in the art to increase catalase activity to protect melanocytes; however, this will similarly support T cell longevity. Thus there is a dire need for treatment measures that can inhibit and preferentially invert depigmentation. The trials above show that the peptide region QPGVLIQVYEG (residues 435-445 of SEQ ID NO: 5) is crucial for this response. The trials not only implicate HSP70i in vitiligo, but provide a mechanism by which the autoimmune response is activated and maintained. In knock-out animals, depigmentation could not be established with or without wild-type, or mutant HSP70i. Therefore, it is now believed that depigmentation is fully dependent on CDS cytotoxic T cells. Using HSP70i expressing variants to the DC binding peptide QPGVLIQVYEG (residues 435-445 of SEQ ID NO: 5) in vaccinations, therapeutic measures can be established to reduce or prevent autoimmune diseases including vitiligo, for which effective measures do not exist to date.

In view of the above, a natural, human HSP70i derived peptide that is believed to be pivotal to depigmentation has the sequence: QPGVLIQVYEG (residues 435-445 of SEQ ID NO: 5). The mutant for which autoimmune-inhibiting properties were investigated is APGVLIQVYEG (residues 435-445 of SEQ ID NO: 6). Both depigmentation-enhancing and depigmentation-inhibiting properties are seen with the encoding sequence incorporated into a plasmid containing the full HSP70i eDNA sequence.

Although the invention has been described in terms of the peptide comprising the sequence APGVLIQVYEG (residues 435-445 of SEQ ID NO: 6), other peptides derived from the inducible heat shock protein 70 may be used for treating autoimmune diseases and are therefore within the scope of this invention. These autoimmune-inhibiting peptides are characterized by their ability to reduce or prevent activation of DCs due to HSP70i. Such autoimmune-inhibiting peptides are preferably adapted to a vaccine comprising the peptide derived from HSP70i and a plasmid containing the full HSP70i DNA sequence encoding the peptide. The resulting vaccine may be combined with a vaccine administration device to form a vaccination kit. An example of the administration device is, but should not be limited to, a gene gun.

According to a preferred aspect of the invention, human patients susceptible to or suffering from autoimmune diseases can be treated using vaccines formed from the autoimmune-inhibiting peptides. In the case of vitiligo, it is believed that the patients will experience reduced depigmentation in their skin once vaccinated with the vaccine as described above.

While the invention has been described in terms of specific embodiments, it is apparent that other forms could be adopted by one skilled in the art. For example, the specific peptide derived from the HSP70i could differ from that shown, and materials and processes other than those noted could be used. Therefore, the scope of the invention is to be limited only by the following claims.

The invention claimed is:

1. A method of treating vitiligo in a subject, the method comprising: administering a composition to the subject comprising DNA encoding a variant inducible heat shock protein 70 (HSP70i) comprising the amino acid sequence APGVLIQVYEG in the dendritic cell binding region thereof corresponding to amino acids 435-445 of SEQ ID NO: 6.

2. The method of claim 1, wherein the composition is characterized by its ability to reduce activation of dendritic cells.

3. The method of claim 1, wherein the administrating step is performed with a gene gun.

4. The method according to claim 1, wherein the subject is genetically prone to vitiligo.

5. A method of treating vitiligo in a subject, the method comprising: administering a composition to the subject comprising a variant HSP70i gene product comprising the amino acid sequence APGVLIQVYEG in the dendritic cell activating region thereof corresponding to amino acids 435-445 of SEQ ID NO: 6.

6. The method according to claim 5, wherein the subject is genetically prone to vitiligo.

* * * * *

UNITED STATES PATENT AND TRADEMARK OFFICE
CERTIFICATE OF CORRECTION

PATENT NO. : 10,829,526 B2
APPLICATION NO. : 15/791609
DATED : November 10, 2020
INVENTOR(S) : I. Caroline Le Poole et al.

Page 1 of 1

It is certified that error appears in the above-identified patent and that said Letters Patent is hereby corrected as shown below:

In the Specification

At Column 1, Line 17:
"This invention was made with government support under Grant/Contract No. AR054749 awarded by the National Institute of Health. The Government has certain rights in the invention."

Should be:
"This invention was made with government support under grant numbers AR054749 and CA191317 awarded by the National Institutes of Health. The government has certain rights in the invention."

Signed and Sealed this
Fourth Day of February, 2025

Coke Morgan Stewart
*Acting Director of the United States Patent and Trademark Office*

SEQUENCE LISTING

<160> NUMBER OF SEQ ID NOS: 8

<210> SEQ ID NO 1
<211> LENGTH: 1926
<212> TYPE: DNA
<213> ORGANISM: Homo sapiens

<400> SEQUENCE: 1

| | | | | | |
|---|---|---|---|---|---|
| atggccaaag | ccgcggcgat | cggcatcgac | ctgggcacca | cctactcctg | cgtgggggtg | 60 |
| ttccaacacg | gcaaggtgga | gatcatcgcc | aacgaccagg | gcaaccgcac | caccccagc | 120 |
| tacgtggcct | tcacggacac | cgagcggctc | atcggggatg | cggccaagaa | ccaggtggcg | 180 |
| ctgaacccgc | agaacaccgt | gtttgacgcg | aagcggctga | tcggccgcaa | gttcggcgac | 240 |
| ccggtggtgc | agtcggacat | gaagcactgg | cctttccagg | tgatcaacga | cggagacaag | 300 |
| cccaaggtgc | aggtgagcta | caaggggac | accaaggcat | ctacccga | ggagatctcg | 360 |
| tccatggtgc | tgaccaagat | gaaggagatc | gccgaggcgt | acctgggcta | cccggtgacc | 420 |
| aacgcggtgg | tcaccgtgcc | ggcctacttc | aacgactcgc | agcgccaggc | caccaaggat | 480 |
| gcgggtgtga | tcgcggggct | caacgtgctg | cggatcatca | acgagcccac | ggccgccgcc | 540 |
| atcgcctacg | gcctggacag | aacgggcaag | ggggagcgca | acgtgctcat | ctttgacctg | 600 |
| ggcgggggca | ccttcgacgt | gtccatcctg | acgatcgacg | acggcatctt | cgaggtgaag | 660 |
| gccacggccg | gggacacccca | cctgggtggg | gaggactttg | acaacaggct | ggtgaaccac | 720 |
| ttcgtggagg | agttcaagag | aaaacacaag | aaggacatca | gccagaacaa | gcagccgtg | 780 |
| aggcggctgc | gcaccgcctg | cgagagggcc | aagaggaccc | tgtcgtccag | cacccaggcc | 840 |
| agcctggaga | tcgactccct | gtttgagggc | atcgacttct | acacgtccat | caccagggcg | 900 |
| aggttcgagg | agctgtgctc | cgacctgttc | cgaagcaccc | tggagcccgt | ggagaaggct | 960 |
| ctgcgcgacg | ccaagctgga | caaggcccag | attcacgacc | tggtcctggt | cgggggctcc | 1020 |
| acccgcatcc | ccaaggtgca | gaagctgctg | caggacttct | tcaacgggcg | cgacctgaac | 1080 |
| aagagcatca | cccccgacga | ggctgtggcc | tacggggcgg | cggtgcaggc | ggccatcctg | 1140 |
| atggggaca | agtccgagaa | cgtgcaggac | ctgctgctgc | tggacgtggc | tcccctgtcg | 1200 |
| ctggggctgg | agacggccgg | aggcgtgatg | actgccctga | tcaagcgcaa | ctccaccatc | 1260 |
| cccaccaagc | agacgcagat | cttcaccacc | tactccgaca | accaacccgg | ggtgctgatc | 1320 |
| caggtgtacg | agggcgagag | ggccatgacg | aaagacaaca | atctgttggg | gcgcttcgag | 1380 |
| ctgagcggca | tccctccggc | cccaggggc | gtgccccaga | tcgaggtgac | cttcgacatc | 1440 |
| gatgccaacg | gcatcctgaa | cgtcacggcc | acggacaaga | gcaccggcaa | ggccaacaag | 1500 |
| atcaccatca | ccaacgacaa | gggccgcctg | agcaaggagg | agatcgagcg | catggtgcag | 1560 |
| gaggcggaga | agtacaaagc | ggaggacgag | gtgcagcgcg | agagggtgtc | agccaagaac | 1620 |
| gccctggagt | cctacgcctt | caacatgaag | agcgccgtgg | aggatgaggg | gctcaagggc | 1680 |
| aagatcagcg | aggccgacaa | gaagaaggtg | ctggacaagt | gtcaagaggt | catctcgtgg | 1740 |
| ctggacgcca | acaccttggc | cgagaaggac | gagtttgagc | acaagaggaa | ggagctggag | 1800 |
| caggtgtgta | accccatcat | cagcggactg | taccagggtg | ccggtggtcc | cgggcctggg | 1860 |
| ggcttcgggg | ctcagggtcc | caaggagggg | tctgggtcag | gccccaccat | tgaggaggta | 1920 |
| gattag | | | | | | 1926 |

<210> SEQ ID NO 2
<211> LENGTH: 1926

```
<212> TYPE: DNA
<213> ORGANISM: Artificial Sequence
<220> FEATURE:
<223> OTHER INFORMATION: Synthetic
<220> FEATURE:
<221> NAME/KEY: Mutation
<222> LOCATION: (1303)..(1304)

<400> SEQUENCE: 2
atggccaaag ccgcggcgat cggcatcgac ctgggcacca cctactcctg cgtgggggtg      60
ttccaacacg gcaaggtgga gatcatcgcc aacgaccagg gcaaccgcac caccccagc     120
tacgtggcct tcacggacac cgagcggctc atcggggatg cggccaagaa ccaggtggcg    180
ctgaacccgc agaacaccgt gtttgacgcg aagcggctga tcggccgcaa gttcggcgac    240
ccggtggtgc agtcggacat gaagcactgg cctttccagg tgatcaacga cggagacaag    300
cccaaggtgc aggtgagcta aggggggac accaaggcat ctaccccga ggagatctcg     360
tccatggtgc tgaccaagat gaaggagatc gccgaggcgt acctgggcta cccggtgacc    420
aacgcggtgg tcaccgtgcc ggcctacttc aacgactcgc agcgccaggc caccaaggat    480
gcgggtgtga tcgcggggct caacgtgctg cggatcatca cgagcccac ggccgccgcc     540
atcgcctacg gctggacag aacgggcaag ggggagcgca cgtgctcat ctttgacctg      600
ggcggggca cttcgacgt gtccatcctg acgatcgacg acggcatctt cgaggtgaag      660
gccacggccg gggacaccca cctgggtggg gaggactttg acaacaggct ggtgaaccac    720
ttcgtggagg agttcaagag aaaacacaag aaggacatca gccagaacaa gcgagccgtg    780
aggcggctgc gcaccgcctg cgagagggcc aagaggaccc tgtcgtccag cacccaggcc    840
agcctggaga tcgactccct gtttgagggc atcgacttct acacgtccat caccagggcg    900
aggttcgagg agctgtgctc cgacctgttc cgaagcaccc tggagcccgt ggagaaggct    960
ctgcgcgacg ccaagctgga caaggcccag attcacgacc tggtcctggt cggggctcc   1020
acccgcatcc ccaaggtgca gaagctgctg caggacttct tcaacgggcg cgacctgaac   1080
aagagcatca ccccgacga ggctgtggcc tacggggcgg cggtgcaggc ggccatcctg    1140
atgggggaca gtccgagaa cgtgcaggac ctgctgctgc tggacgtggc tcccctgtcg   1200
ctggggctgg agacggccgg aggcgtgatg actgccctga tcaagcgcaa ctccaccatc   1260
cccaccaagc agacgcagat cttcaccacc tactccgaca cgcacccgg ggtgctgatc    1320
caggtgtacg agggcgagag ggccatgacg aaagacaaca atctgttggg gcgcttcgag   1380
ctgagcggca tccctccggc ccccagggc gtgccccaga tcgaggtgac cttcgacatc     1440
gatgccaacg gcatcctgaa cgtcacggcc acggacaaga gcaccggcaa ggccaacaag   1500
atcaccatca ccaacgacaa gggccgcctg agcaaggagg agatcgagcg catggtgcag   1560
gaggcggaga agtacaaagc ggaggacgag gtgcagcgcg agagggtgtc agccaagaac   1620
gccctggagt cctacgcctt caacatgaag agcgccgtgg aggatgaggg gctcaagggc   1680
aagatcagcg aggccgacaa gaagaaggtg ctggacaagt gtcaagaggt catctcgtgg   1740
ctggacgcca acaccttggc cgagaaggac gagtttgagc acaagaggaa ggagctggag   1800
caggtgtgta accccatcat cagcggactg taccagggtg ccggtggtcc cgggcctggg   1860
ggcttcgggg ctcagggtcc caagggaggg tctgggtcag gccccaccat tgaggaggta   1920
gattag                                                              1926

<210> SEQ ID NO 3
<211> LENGTH: 1926
```

<212> TYPE: DNA
<213> ORGANISM: Artificial Sequence
<220> FEATURE:
<223> OTHER INFORMATION: Synthetic
<220> FEATURE:
<221> NAME/KEY: Mutation
<222> LOCATION: (1325)..(1325)
<220> FEATURE:
<221> NAME/KEY: Mutation
<222> LOCATION: (1327)..(1328)

<400> SEQUENCE: 3

| | |
|---|---|
| atggccaaag ccgcggcgat cggcatcgac ctgggcacca cctactcctg cgtgggggtg | 60 |
| ttccaacacg gcaaggtgga gatcatcgcc aacgaccagg gcaaccgcac cacccccagc | 120 |
| tacgtggcct tcacggacac cgagcggctc atcggggatg cggccaagaa ccaggtggcg | 180 |
| ctgaacccgc agaacaccgt gtttgacgcg aagcggctga tcggccgcaa gttcggcgac | 240 |
| ccggtggtgc agtcggacat gaagcactgg cctttccagg tgatcaacga cggagacaag | 300 |
| cccaaggtgc aggtgagcta caaggggac accaaggcat tctacccga ggagatctcg | 360 |
| tccatggtgc tgaccaagat gaaggagatc gccgaggcgt acctgggcta cccggtgacc | 420 |
| aacgcggtgg tcaccgtgcc ggcctacttc aacgactcgc agcgccaggc caccaaggat | 480 |
| gcgggtgtga tcgcggggct caacgtgctg cggatcatca cgagcccac ggccgccgcc | 540 |
| atcgcctacg gcctggacag aacgggcaag ggggagcgca acgtgctcat ctttgacctg | 600 |
| ggcggggca ccttcgacgt gtccatcctg acgatcgacg acggcatctt cgaggtgaag | 660 |
| gccacggccg gggacaccca cctgggtggg gaggactttg acaacaggct ggtgaaccac | 720 |
| ttcgtggagg agttcaagag aaaacacaag aaggacatca gccagaacaa gcgagccgtg | 780 |
| aggcggctgc gcaccgcctg cgagagggcc aagaggaccc tgtcgtccag cacccaggcc | 840 |
| agcctggaga tcgactccct gtttgagggc atcgacttct acacgtccat caccagggcg | 900 |
| aggttcgagg agctgtgctc cgacctgttc cgaagcaccc tggagcccgt ggagaaggct | 960 |
| ctgcgcgacg ccaagctgga caaggcccag attcacgacc tggtcctggt cgggggctcc | 1020 |
| acccgcatcc ccaaggtgca gaagctgctg caggacttct tcaacgggcg cgacctgaac | 1080 |
| aagagcatca accccgacga ggctgtggcc tacggggcgg cggtgcaggc ggccatcctg | 1140 |
| atggggaca gtccgagaa cgtgcaggac ctgctgctgc tggacgtggc tcccctgtcg | 1200 |
| ctggggctgg agacggccgg aggcgtgatg actgccctga tcaagcgcaa ctccaccatc | 1260 |
| cccaccaagc agacgcagat cttcaccacc tactccgaca accaaccgg ggtgctgatc | 1320 |
| caggcggtcg agggcgagag ggccatgacg aaagacaaca atctgttggg gcgcttcgag | 1380 |
| ctgagcggca tccctccggc cccagggggc gtgccccaga tcgaggtgac cttcgacatc | 1440 |
| gatgccaacg gcatcctgaa cgtcacggcc acggacaaga gcaccggcaa ggccaacaag | 1500 |
| atcaccatca ccaacgacaa gggccgcctg agcaaggagg agatcgagcg catggtgcag | 1560 |
| gaggcggaga agtacaaagc ggaggacgag gtgcagcgcg agagggtgtc agccaagaac | 1620 |
| gccctggagt cctacgcctt caacatgaag agcgccgtgg aggatgaggg gctcaagggc | 1680 |
| aagatcagcg aggccgacaa gaagaaggtg ctggacaagt gtcaagaggt catctcgtgg | 1740 |
| ctggacgcca acaccttggc cgagaaggac gagtttgagc acaagaggaa ggagctggag | 1800 |
| caggtgtgta accccatcat cagcggactg taccagggtg ccgtggtcc cgggcctggg | 1860 |
| ggcttcgggg ctcagggtcc caagggaggg tctgggtcag gccccaccat tgaggaggta | 1920 |
| gattag | 1926 |

<210> SEQ ID NO 4
<211> LENGTH: 1926
<212> TYPE: DNA
<213> ORGANISM: Artificial Sequence
<220> FEATURE:
<223> OTHER INFORMATION: Synthetic
<220> FEATURE:
<221> NAME/KEY: Mutation
<222> LOCATION: (1312)..(1313)
<220> FEATURE:
<221> NAME/KEY: Mutation
<222> LOCATION: (1318)..(1319)

<400> SEQUENCE: 4

```
atggccaaag ccgcggcgat cggcatcgac ctgggcacca cctactcctg cgtgggggtg      60
ttccaacacg gcaaggtgga gatcatcgcc aacgaccagg gcaaccgcac cacccccagc     120
tacgtggcct tcacggacac cgagcggctc atcggggatg cggccaagaa ccaggtggcg     180
ctgaacccgc agaacaccgt gtttgacgcg aagcggctga tcggccgcaa gttcggcgac     240
ccggtggtgc agtcggacat gaagcactgg ccttttccagg tgatcaacga cggagacaag     300
cccaaggtgc aggtgagcta aggggggac accaaggcat ctaccccga ggagatctcg       360 tccatggtgc tgaccaagat gaaggagatc gccgaggcgt acctgggcta cccggtgacc     420
aacgcggtgg tcaccgtgcc ggcctacttc aacgactcgc agcgccaggc caccaaggat     480
gcgggtgtga tcgcggggct caacgtgctg cggatcatca acgagcccac ggccgccgcc     540
atcgcctacg gcctggacag aacgggcaag ggggagcgca acgtgctcat ctttgacctg     600 ggcggggca ccttcgacgt gtccatcctg acgatcgacg acggcatctt cgaggtgaag     660
gccacggccg ggacacccca cctgggtggg gaggactttg acaacaggct ggtgaaccac     720
ttcgtggagg agttcaagag aaaacacaag aaggacatca gccagaacaa gcgagccgtg     780
aggcggctgc gcaccgcctg cgagagggcc aagaggaccc tgtcgtccag cacccaggcc     840
agcctggaga tcgactccct gtttgagggc atcgacttct acacgtccat caccaggcg     900 aggttcgagg agctgtgctc cgacctgttc cgaagcaccc tggagcccgt ggagaaggct     960
ctgcgcgacg ccaagctgga caaggcccag attcacgacc tggtcctggt cggggggctcc   1020 acccgcatcc ccaaggtgca gaagctgctg caggacttct tcaacgggcg cgacctgaac    1080
aagagcatca cccccgacga ggctgtggcc tacggggcgg cggtgcaggc ggccatcctg    1140
atgggggaca gtccgagaa cgtgcaggac ctgctgctgc tggacgtggc tccctgtcg     1200 ctggggctgg agacggccgg aggcgtgatg actgccctga tcaagcgcaa ctccaccatc    1260
cccaccaagc agacgcagat cttcaccacc tactccgaca ccaacccgg gaagctggcc     1320 caggtgtacg agggcgagag ggccatgacg aaagacaaca atctgttggg gcgcttcgag    1380
ctgagcggca tccctccggc ccccaggggc gtgccccaga tcgaggtgac cttcgacatc    1440
gatgccaacg cgatcctgaa cgtcacggcc acggacaaga gcaccggcaa ggccaacaag    1500
atcaccatca ccaacgacaa gggccgcctg agcaaggagg agatcgagcg catggtgcag    1560
gaggcggaga agtacaaagc ggaggacgag gtgcagcgcg agagggtgtc agccaagaac    1620
gccctggagt cctacgcctt caacatgaag agcgccgtgg aggatgaggg gctcaagggc    1680
aagatcagcg aggccgacaa gaagaaggtg ctggacaagt gtcaagaggt catctcgtgg    1740
ctggacgcca acaccttggc cgagaaggac gagtttgagc acaagaggaa ggagctggag    1800
caggtgtgta accccatcat cagcggactg taccagggtg ccggtggtcc cgggcctggg    1860
ggcttcgggg ctcagggtcc caagggaggg tctgggtcag gccccaccat tgaggagta    1920
```

```
gattag                                                         1926
```

<210> SEQ ID NO 5
<211> LENGTH: 641
<212> TYPE: PRT
<213> ORGANISM: Homo sapiens

<400> SEQUENCE: 5

```
Met Ala Lys Ala Ala Ile Gly Ile Asp Leu Gly Thr Thr Tyr Ser
 1               5                  10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
 50                  55                  60

Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Asp Thr Lys
                100                 105                 110

Ala Phe Tyr Pro Glu Glu Ile Ser Ser Met Val Leu Thr Lys Met Lys
            115                 120                 125

Glu Ile Ala Glu Ala Tyr Leu Gly Tyr Pro Val Thr Asn Ala Val Val
            130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
            195                 200                 205

Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
            275                 280                 285

Glu Gly Ile Asp Phe Tyr Thr Ser Ile Thr Arg Ala Arg Phe Glu Glu
            290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
            355                 360                 365
```

```
Val Ala Tyr Gly Ala Ala Val Gln Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
                435                 440                 445

Met Thr Lys Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Lys Tyr Lys Ala Glu
        515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
                580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
        610                 615                 620

Gln Gly Pro Lys Gly Gly Ser Gly Ser Gly Pro Thr Ile Glu Glu Val
625                 630                 635                 640

Asp

<210> SEQ ID NO 6
<211> LENGTH: 641
<212> TYPE: PRT
<213> ORGANISM: Artificial Sequence
<220> FEATURE:
<223> OTHER INFORMATION: Synthetic
<220> FEATURE:
<221> NAME/KEY: Mutation
<222> LOCATION: (435)..(435)

<400> SEQUENCE: 6

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
    50                  55                  60
```

```
Asn Thr Val Phe Asp Ala Lys Arg Leu Ile Gly Arg Lys Phe Gly Asp
 65                  70                  75                  80

Pro Val Val Gln Ser Asp Met Lys His Trp Pro Phe Gln Val Ile Asn
                 85                  90                  95

Asp Gly Asp Lys Pro Lys Val Gln Val Ser Tyr Lys Gly Asp Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
                180                 185                 190

Arg Asn Val Leu Ile Phe Asp Leu Gly Gly Thr Phe Asp Val Ser
            195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
            420                 425                 430

Asp Asn Ala Pro Gly Val Leu Ile Gln Val Tyr Glu Gly Glu Arg Ala
        435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
```

-continued

```
                485                 490                 495
Lys Ala Asn Lys Ile Thr Ile Thr Asn Asp Lys Gly Arg Leu Ser Lys
                500                 505                 510
Glu Glu Ile Glu Arg Met Val Gln Glu Ala Lys Tyr Lys Ala Glu
                515                 520                 525
Asp Glu Val Gln Arg Glu Arg Val Ser Ala Lys Asn Ala Leu Glu Ser
        530                 535                 540
Tyr Ala Phe Asn Met Lys Ser Ala Val Glu Asp Glu Gly Leu Lys Gly
545                 550                 555                 560
Lys Ile Ser Glu Ala Asp Lys Lys Val Leu Asp Lys Cys Gln Glu
                565                 570                 575
Val Ile Ser Trp Leu Asp Ala Asn Thr Leu Ala Glu Lys Asp Glu Phe
                580                 585                 590
Glu His Lys Arg Lys Glu Leu Glu Gln Val Cys Asn Pro Ile Ile Ser
        595                 600                 605
Gly Leu Tyr Gln Gly Ala Gly Gly Pro Gly Pro Gly Gly Phe Gly Ala
        610                 615                 620
Gln Gly Pro Lys Gly Gly Ser Gly Ser Gly Pro Thr Ile Glu Glu Val
625                 630                 635                 640
Asp
```

<210> SEQ ID NO 7
<211> LENGTH: 641
<212> TYPE: PRT
<213> ORGANISM: Artificial Sequence
<220> FEATURE:
<223> OTHER INFORMATION: Synthetic
<220> FEATURE:
<221> NAME/KEY: Mutation
<222> LOCATION: (442)..(443)

<400> SEQUENCE: 7

```
Met Ala Lys Ala Ala Ala Ile Gly Ile Asp Leu Gly Thr Thr Tyr Ser
1               5                   10                  15
Cys Val Gly Val Phe Gln His Gly Lys Val Glu Ile Ile Ala Asn Asp
                20                  25                  30
Gln Gly Asn Arg Thr Thr Pro Ser Tyr Val Ala Phe Thr Asp Thr Glu
        35                  40                  45
Arg Leu Ile Gly Asp Ala Ala Lys Asn Gln Val Ala Leu Asn Pro Gln
    50                  55                  60
Asn Thr Val Phe Asp Ala Lys Arg Leu Ile Gly Arg Lys Phe Gly Asp
65                  70                  75                  80
Pro Val Val Gln Ser Asp Met Lys His Trp Pro Phe Gln Val Ile Asn
                85                  90                  95
Asp Gly Asp Lys Pro Lys Val Gln Val Ser Tyr Lys Gly Asp Thr Lys
                100                 105                 110
Ala Phe Tyr Pro Glu Glu Ile Ser Ser Met Val Leu Thr Lys Met Lys
        115                 120                 125
Glu Ile Ala Glu Ala Tyr Leu Gly Tyr Pro Val Thr Asn Ala Val Val
    130                 135                 140
Thr Val Pro Ala Tyr Phe Asn Asp Ser Gln Arg Gln Ala Thr Lys Asp
145                 150                 155                 160
Ala Gly Val Ile Ala Gly Leu Asn Val Leu Arg Ile Ile Asn Glu Pro
                165                 170                 175
Thr Ala Ala Ala Ile Ala Tyr Gly Leu Asp Arg Thr Gly Lys Gly Glu
                180                 185                 190
```

```
Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
        210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                    245                 250                 255

Lys Arg Ala Val Arg Arg Leu Arg Thr Ala Cys Glu Arg Ala Lys Arg
                260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
        290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
                340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
        370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Ala Val Glu Gly Glu Arg Ala
        435                 440                 445

Met Thr Lys Asp Asn Asn Leu Leu Gly Arg Phe Glu Leu Ser Gly Ile
        450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Lys Tyr Lys Ala Glu
        515                 520                 525

Asp Glu Val Gln Arg Glu Arg Val Ser Ala Lys Asn Ala Leu Glu Ser
        530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
                580                 585                 590

Glu His Lys Arg Lys Glu Leu Glu Gln Val Cys Asn Pro Ile Ile Ser
        595                 600                 605
```

```
Gly Leu Tyr Gln Gly Ala Gly Gly Pro Gly Pro Gly Gly Phe Gly Ala
    610                 615                 620
Gln Gly Pro Lys Gly Gly Ser Gly Ser Gly Pro Thr Ile Glu Glu Val
625                 630                 635                 640
Asp

<210> SEQ ID NO 8
<211> LENGTH: 641
<212> TYPE: PRT
<213> ORGANISM: Artificial Sequence
<220> FEATURE:
<223> OTHER INFORMATION: Synthetic
<220> FEATURE:
<221> NAME/KEY: Mutation
<222> LOCATION: (438)..(438)
<220> FEATURE:
<221> NAME/KEY: Mutation
<222> LOCATION: (440)..(440)

<400> SEQUENCE: 8

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Asp Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
```

```
            290                 295                 300
Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
                340                 345                 350

Phe Phe Asn Gly Arg Asp Leu Asn Lys Ser Ile Asn Pro Asp Glu Ala
                355                 360                 365

Val Ala Tyr Gly Ala Ala Val Gln Ala Ala Ile Leu Met Gly Asp Lys
                370                 375                 380

Ser Glu Asn Val Gln Asp Leu Leu Leu Leu Asp Val Ala Pro Leu Ser
385                 390                 395                 400

Leu Gly Leu Glu Thr Ala Gly Gly Val Met Thr Ala Leu Ile Lys Arg
                        405                 410                 415

Asn Ser Thr Ile Pro Thr Lys Gln Thr Gln Ile Phe Thr Thr Tyr Ser
                420                 425                 430

Asp Asn Gln Pro Gly Lys Leu Ala Gln Val Tyr Glu Gly Glu Arg Ala
                435                 440                 445

Met Thr Lys Asp Asn Asn Leu Leu Gly Arg Phe Glu Leu Ser Gly Ile
                450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Glu Lys Tyr Lys Ala Glu
                515                 520                 525

Asp Glu Val Gln Arg Glu Arg Val Ser Ala Lys Asn Ala Leu Glu Ser
                530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Lys Val Leu Asp Lys Cys Gln Glu
                565                 570                 575

Val Ile Ser Trp Leu Asp Ala Asn Thr Leu Ala Glu Lys Asp Glu Phe
                580                 585                 590

Glu His Lys Arg Lys Glu Leu Glu Gln Val Cys Asn Pro Ile Ile Ser
                595                 600                 605

Gly Leu Tyr Gln Gly Ala Gly Gly Pro Gly Pro Gly Gly Phe Gly Ala
                610                 615                 620

Gln Gly Pro Lys Gly Gly Ser Gly Ser Gly Pro Thr Ile Glu Glu Val
625                 630                 635                 640

Asp
```